United States Patent
Soar

(10) Patent No.: US 8,981,796 B2
(45) Date of Patent: Mar. 17, 2015

(54) WIRELESS METHOD AND APPARATUS FOR DETECTING DAMAGE IN CERAMIC BODY ARMOR

(75) Inventor: Roger J. Soar, Kelowna (CA)

(73) Assignee: Cynetic Designs Ltd. (CA)

( * ) Notice: Subject to any disclaimer, the term of this patent is extended or adjusted under 35 U.S.C. 154(b) by 318 days.

(21) Appl. No.: 13/695,158

(22) PCT Filed: Apr. 29, 2011

(86) PCT No.: PCT/CA2011/000493
§ 371 (c)(1), (2), (4) Date: Oct. 29, 2012

(87) PCT Pub. No.: WO2011/134068
PCT Pub. Date: Nov. 3, 2011

(65) Prior Publication Data
US 2013/0043888 A1 Feb. 21, 2013

Related U.S. Application Data

(60) Provisional application No. 61/282,972, filed on Apr. 30, 2010.

(51) Int. Cl.
*G01R 27/28* (2006.01)
*F41H 1/02* (2006.01)
*F41H 5/04* (2006.01)
*F41J 5/04* (2006.01)
*F41J 5/14* (2006.01)
*G01N 27/02* (2006.01)

(52) U.S. Cl.
CPC ............... *F41H 1/02* (2013.01); *F41H 5/0428* (2013.01); *F41J 5/04* (2013.01); *F41J 5/14* (2013.01); *G01N 27/023* (2013.01)
USPC .......................... 324/655; 324/654; 324/71.1

(58) Field of Classification Search
USPC .............. 324/654, 655, 663–665, 71.1, 76.51
See application file for complete search history.

(56) References Cited

U.S. PATENT DOCUMENTS

| | | | |
|---|---|---|---|
| 7,040,139 B2 * | 5/2006 | Sunshine | 73/23.2 |
| 7,180,302 B2 | 2/2007 | Kelsey et al. | |
| 7,805,767 B2 | 10/2010 | McElroy et al. | |
| 2009/0043516 A1 | 2/2009 | Liu et al. | |
| 2012/0222543 A1 * | 9/2012 | Meitzler et al. | 89/36.02 |

* cited by examiner

*Primary Examiner* — Vincent Q Nguyen
(74) *Attorney, Agent, or Firm* — Antony C. Edwards

(57) ABSTRACT

A wireless damage detector for ceramic armor plates includes an interrogator and a body armor ceramic plate. The interrogator includes an inductive primary coil having a resonant frequency. The plate includes a corresponding inductive secondary coil adapted to cooperate with the primary coil when the interrogator is positioned in an interrogation position wirelessly adjacent the plate. When in the interrogation position, the primary and secondary coils are inductively coupled, that is, form an inductive coupling, when the primary coil is energized at the resonant frequency. The plate includes at least one self-contained frangible continuity circuit electrically connected to the secondary coil. The inductive coupling induces an electrical current flow in the continuity circuit when the circuit is undamaged. A detector cooperates with the primary and secondary coils when the interrogator is in the interrogation position. The detector detects the inductive coupling. An indicator cooperates with the detector.

33 Claims, 14 Drawing Sheets

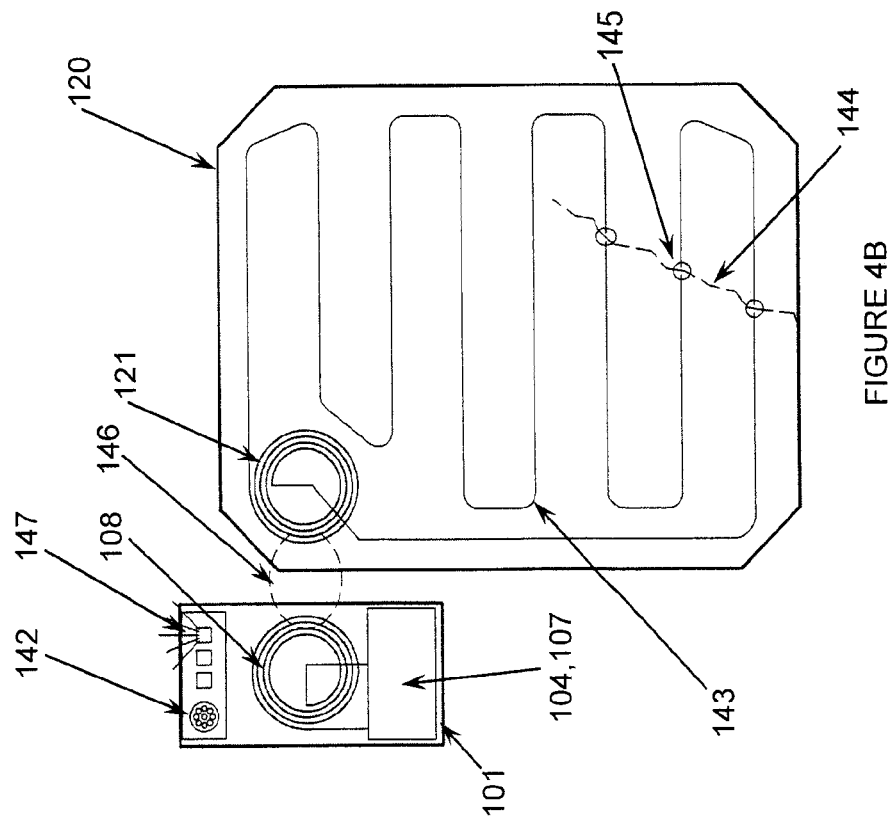
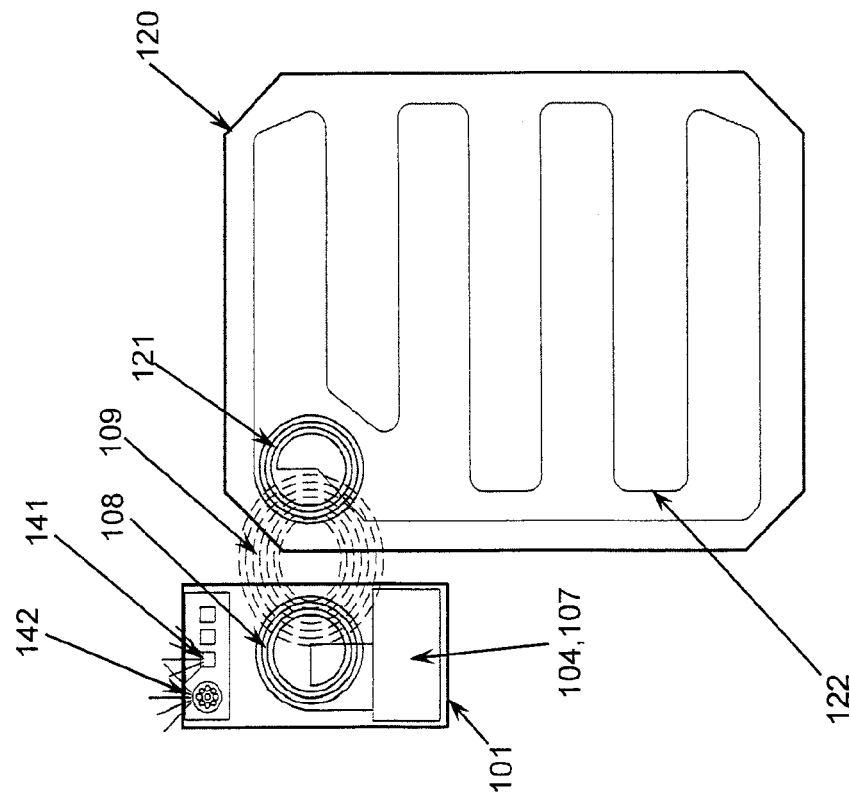

| Coil Separation Distance mm | Resonant Frequency KHz | Impedance Z Ohms | Current ma |
|---|---|---|---|
| Self Resonance | 145 | 136 | 5.6 |
| 15.0 | 147 | 130 | 5.7 |
| 10.0 | 150 | 133 | 5.8 |
| 6.0 | 157 | 123 | 6.0 |
| 4.0 | 168 | 112 | 7.8 |
| 2.0 | 206 | 79 | 8.2 |
| 1.0 | 222 | 59 | 9.5 |

Figure 7a. Frequency, impedance and current measurements for an interrogator 145KHz primary inductive coil tank circuit influenced by the mutual inductance of a ceramic plate secondary inductive coil.

WIRELESS METHOD AND APPARATUS FOR DETECTING DAMAGE IN CERAMIC BODY ARMOR

FIELD OF THE INVENTION

The invention relates to personal ceramic/composite armor systems and a method to determine the integrity of the ceramic plate component while in the battlefield environment using rugged non-contact inspection equipment that does not require formal training to operate. The equipment allows non-contact inspection of body armor plates without the use of wires or connectors and is to be used as a field tool to pre-screen plates to determine if the plate should be sent for more involved inspection using x-ray equipment.

BACKGROUND OF THE INVENTION

The modern soldier is equipped with an ensemble of protective clothing. Part of the ensemble is ballistic protection which is typically comprised of a soft ballistic vest that provides fragmentation and hand gun protection. The ballistic vest has large plate pockets on the front and rear into which can be inserted hard armor plates that protect against high velocity ballistic threats. A recurring issue for ballistic protection ceramic body armor plates such as the SAPI (Small Arms Protective Insert) and ESAPI (Enhanced Small Arms Protective Insert) and other configurations of body armor with a ceramic strike face, is that it is very difficult to determine the integrity of the ceramic plate when they are in service. To obtain optimal ballistic protection and performance from a ceramic plate it is necessary that the ceramic strike face be free from cracks and fractures that would compromise the ability of the ceramic to defeat a ballistic threat when it is impacted.

When plates are in service and especially when in theatre they are subject to the rigours of the battlefield. The plates are very heavy with a weight that ranges between 2.5 and 4.5 kilograms each, depending on size and construction material, with usually two plates provided per vest. As a result of their weight, the plates are repeatedly banged and struck against hard objects. Even through such simple activities as when the vest is taken off and put down on the ground the ceramic may be damaged. The plates are constructed with a fabric or plastic cover over the entire plate and depending on the design may have thin layers of additional materials such as polycarbonate, plastics or foam on the ceramic strike face to afford it some protection from bumps. All these layers and covers make it impossible to determine the integrity of the ceramic and whether or not the plate should stay in service when the plate is inspected visually. Conventional means of Non Destructive Technology (NDT) that are used to inspect composite/ceramic structures include air coupled and immersion ultrasonics, Infrared and laser thermography, eddy current and digital x-ray require involved equipment and facilities or specialized technical skills. In addition several of these techniques cannot be used when a plate has any type of protective cover on it as the ceramic component needs to be directly accessed. As a body armor plate cannot be stripped of its protective cover to see if it may be damaged, the inspection method being promoted for in-field inspection and being implemented by the US Army is to inspect armor with portable digital x-ray systems. Even small digital x-ray testing capability however is not typically found in theatre and definitely not at forward operating bases where the hard armor is placed into daily active service to protect the soldiers. To accommodate the inspections that are made away from the forward battlefield, increased supplies of hard armor plates must be purchased to provide sufficient stock for rotation through inspection. A test method must therefore be implemented that can be used by the soldier, takes less than 5 seconds for a result indication, is not an inconvenience to the soldier, and is rugged and reliable.

Prior art does exist for determining ceramic plate integrity, however for a number of reasons it is difficult to apply the prior art devices in the battlefield.

Kelsey (U.S. Patent 2007/7,180,302) "Method and system for determining cracks and broken components in armor", describes how a ceramic plate can be screened with conductive traces of various patterns. The conductive circuit must be accessed by a user at electrical contacts provided in the system. The circuit is arranged so that damage, such as cracks that occurs within the ceramic component, can propagate into the conductive material forming the circuit and thereby cause a rupture in the conductive circuit. A voltage source or electrical probe such as an ohmmeter is used to measure the conductive circuit resistance that is then checked against an expected resistive value. The results are used to determine if the ceramic armor component is in operable condition.

Kelsey et al describe an electrical connector that is preferably integrated into or at an edge of the armor system. The connector or contact pads must have an elastomeric seal or dust cover to protect the terminals to which a meter must be connected. There are several problems with the implementation within an in theatre environment. Firstly, physical connection must be made to the plate for it to be inspected. The proposed connector must therefore be designed such that it can withstand general use and abuse associated with the weight and impacts of an armor plate. The connector must be designed to be sufficiently robust such that it cannot be knocked off or damaged during insertion of the plate into a vest plate pocket. It must also withstand the repeated insertion of a connector or contact forces required by meter probes without separating the connector from the conductive ink traces on the plate which are very fragile.

Kelsey suggests known values of resistance are used to validate the integrity of the plate. In practice this is compromised by the screening of the conductive ink as the resistive value of the dried ink trace fluctuates depending on the thickness or width of trace and the quality of the electrical contact between the measuring equipment and the plates connector. Further there will always be meter wire and probe management issues within the battlefield environment.

Liu (US Patent Pending 2009/0043516 A1) "Method and Apparatus for Detecting Damage in Armor Structures" describes an inspection system that uses a minimum of four or more peizo-electric transducers that are bonded to either personal body armor or larger armor panels. Using a baseline scan response previously obtained, the plate is analysed to determine if it has structurally changed. The plate is interrogated with a laptop computer although a handheld device has been proposed. The system requires each transducer to be connected externally with cables, with the connection being made in any conventional manner. The system is therefore similar to Kelsey in that it requires external connection for a plate to be tested, albeit with a larger multi-pin connector. It is suggested that the storing of baseline information for individual body armor panels would not be a practical undertaking at a forward operating base making this technology very difficult to implement at the soldier user level. The system also has connector maintenance and interface issues for battlefield implementation as previously discussed with respect to Kelsey.

SUMMARY OF THE INVENTION

In a first embodiment, the invention allows non-contact inspection of body armor plates without the use of wires or connectors. It employs the varying effect on resonant frequency caused by mutual induction between two co-located (proximal or wirelessly adjacent) coils separated by an air gap when one of the coils is magnetically energized with AC power when one or both of the coils can be part of a tuned resonant circuit.

Identified is a passive electronic damage detection circuit that is self-contained upon the ceramic armor plate and does not require an external physical electrical connector or internal battery power to function. To enable this to occur, a continuity circuit is placed upon the ceramic plate that is electrically connected to an inductive coil allowing the ceramic plate to inductively couple to a coil within a handheld interrogator unit.

When the primary coil is in the proximity of a secondary inductive coil that is in a continuous or closed circuit, the mutual inductance created between the primary and secondary coil will affect the impedance and inductive value of the primary coil which in turn will change the resonant frequency of the primary coils tank circuit. The change in the resonant frequency of the primary coil or changes in other characteristic of the resonant circuit is detected by a micro-processor in the primary drive circuit and an indication is provided to the operator.

Two coils are magnetically coupled when an alternating current is passed through one of the coils. When one of the coils is in a tuned circuit (i.e. the primary tank circuit) the electrical characteristics of the tuned circuit are affected by the mutual inductance between the coils as the EMF generated in the secondary coil by the primary coil in turn effects the properties of the primary coil due to reflected impedance from the secondary coil. The mutual inductance between the coils however depends only on the geometrical properties of the two coils such as the number of turns and the radii of the two coils and is independent of the current in the coils.

If the ceramic plates conductive circuit is broken, the impedance and consequent mutual inductive coupling by the secondary coil will be negligible and will not change the resonant frequency of the primary coil tank circuit. In this case the micro-processor will provide a negative indication indicating that the plate may be damaged and should be submitted for further inspection. Feedback on the plates condition is provided by the interrogator unit to the user.

The mutually inductive technique allows armor plates that would be difficult to access or be viewed by the soldier to be inspected without having to remove the plate from the vest. The inductive power can therefore be transmitted through the outer carrier fabric of garments, soft armor panels and the fabric, plastic and foam materials that may be used in the construction of a ceramic armor plate.

A further derivation includes the division of the plate into different sectors, each with its own continuity circuit and secondary coil, allowing the extent of damage to be qualified.

Future applications of the technology that can be implemented in soldier modernisation programs are a miniaturised interrogator primary circuit embedded within the tactical vest and connected to the soldiers' central computer. As an essential part of personal protection, the status of the armor plates integrity can be monitored without the attachment of wires or cables to the plate to ensure it has not been compromised.

In a second embodiment non-contact electrical power inductively applied to a continuity and indicator circuit on the ceramic component of the hard armor plate. One of the iterations of an inductively powered continuity integrity circuit is a series circuit comprised of a secondary coil to receive inductive power from a non-contacting primary coil, a single trace conductive loop printed onto a ceramic plate and an indicator device such as an LED, acoustic emitter or otherwise. To provide a robust circuit to power the indicator, minimal additional support electronics such as a rectifying diode and a current limiting resistor are required.

In use, an interrogator unit that has within it a powered primary inductive coil would brought into proximity and be used to generate a magnetic flux that inductively connects to the secondary coil providing power to the continuity circuit. If the ceramic plate has no cracks the circuit will be continuous and the indicator board will receive power, energizing the LED indicator. If the plate has one or more hairline cracks the circuit will not be continuous and the indicator will not receive power. If a 'no go' indication is provided, the plate can then be removed for more detailed inspection.

As the ceramic circuit does not depend on the measurement of resistance, but the low power flow of electricity, the circuit has little sensitivity to trace resistance. The system allows the plate to be inspected without connectors or cables, the removal of covers, as frequently as is required to assure the user of the plate integrity. This may be done for example within less than five seconds. The circuit is insensitive to manufacturing tolerance and provides positive and negative plate integrity indication only by virtue of circuit continuity.

As the wireless inductive power can pass through the non-magnetic, non-conductive ceramic armor materials, this provides the opportunity to place the secondary inductive coil, secondary conditioning circuit and conductive traces on the back side of the ceramic plate. With the application of suitable adhesives the conductive trace could be broken if the composite backing is pulled away or separates from the back of the ceramic strike face.

An example of a visual indicator would be the use of two or more LED's. The first LED can be used to indicate power is being received by the secondary coil, and that the second conductive trace coil should be indicating, removing any doubt the plate is receiving non-contact power. If the power LED lights and the integrity or conductive LED does not light then the plate must be removed from service for further inspection. If both LED's light then the plate can be left in service.

Alternately only a single LED could be used that only lights when power is available through the entire circuit, the secondary coil and the conductive trace.

A further derivation could be the division of the plate into different sectors each with its own continuity circuit and LED indicator so the extent of damage can be isolated. A coil could also be placed around the outside edge of the plate. All circuits would be powered from a single secondary coil, however an array of LED's would indicate which sector of the plate was damaged and/or how extensive the damage is.

Non visual indicators, for example an audio device which emits an acoustic output when energized introduces the possibility of inspecting the plate when it is inside a vest and not having look at or remove the plate from within the pocket.

In both the first and second embodiments the primary and secondary inductive coils in both the mutually inductive and inductive power transfer implementations work in any environment including being fully submerged and are unaffected by and will operate in environmental conditions such as rain, mud and snow. They also function in the presence of dust, sand, dirt, moisture and POL's.

The conductive trace may be screened directly on the plate or it can be printed on a delicate or frangible media. For both the mutually inductive and inductive power transfer implementations, the conductive loop trace must have matching tensile characteristic to the ceramic such that it will crack with the ceramic. Identified conductive materials would be inks, foils or other conductive materials that will crack when rigidly bonded to a ceramic plate.

Conductive ink may also be placed on a carrier material or media such as a pre-printed paper or other frangible media which would then be adhered to the ceramic surface. Further design and engineering options are conductive inks available with different elasticity.

The secondary coil and continuity circuit can be placed either on the strike face or back side of the ceramic plate with the indicator sub-circuit positioned anywhere on the plate including the front, back or perimeter edge.

Hence to obtain optimal coupling between primary and secondary coils in an air-cored transformer the size and spatial relationships of the coils may be changed, or may employ a ferrite backing to optimise the inductive coupling and the wireless power transfer efficiency. The secondary inductive coil can be of many geometries and sizes but performs best when it is sized to match the size and geometry of the primary coil in the interrogator. The most favourable geometry of the coil is one that is low profile or flat so that it conforms to the plate.

The proximity sensor in the center of the primary coil is triggered when the unit is within the correct distance and centered over the secondary coil on the plate and that magnetic coupling between the primary and the secondary coil can be established. Once the proximity sensor is triggered, the primary coil driver can be turned on. Sensor output can be configured as either an signal LED light to operator or an automatic function. An example proximity sensor would be a hall effect sensor on the interrogator that is triggered by a small magnet or steel disc placed at the center of the secondary coil.

The plate interrogator may be a hand held or optionally a fixture mounted device. It is used to analyse mutual inductance properties or provide power inductively to the secondary coil and plate integrity circuit embedded upon a ceramic armor plate. The interrogator unit for either inductive inspection embodiment has many common attributes.

The interrogator circuit requires an oscillator that determines the frequency at which the inductive circuit will resonate, that feeds into a half or full bridge driver. The output of the driver is connected to an inductive coil and a capacitor which comprise a resonant tank circuit. The inductance value of the coil and the capacitive value of the capacitor are chosen so that a resonant tank circuit of higher voltage than the drive voltage is created when the drive voltage is applied to it. The interrogator system described and its tank circuit can be designed to operate at any resonant frequency however typical frequencies for low power inductive power transfer are the low frequency range of 100-500 KHz, and a high frequency centered around 13.56 MHz range, such as used for RFID devices.

The interrogator housing would typically be constructed from plastic such as ABS or PVC or any other non-magnetic, non-conductive material that does not impede the transmission of the inductive magnetic flux.

The housing may include a corner or edge guide that mechanically helps with positioning of the interrogator over a specified location on the ceramic plate. This would provide optimal coupling and power transfer between the two inductively coupled coils.

The primary coil assembly may have any orientation within the interrogator as long as it can be placed parallel to the plate to be inspected, can be placed on a swivelling head so the operator can determine what angle it is to be used at.

Various audio indicators or visual displays can be placed on the interrogator to provide the operator with feedback of battery power level, main power circuit activation and the response to the inspection of an armor plate if a mutual induction process is utilised. A main power switch provides power to the sleep circuit, a second switch is then pressed to activate the primary coil driver circuit if an automated proximity detection circuit is not employed.

In summary, the system described herein for the wireless detection of damage in a body armor ceramic plate may be characterized in one aspect as including: an interrogator and a body armor ceramic plate, wherein the interrogator includes an inductive primary coil having a resonant frequency and wherein the plate includes a corresponding inductive secondary coil adapted to cooperate with the primary coil when the interrogator is positioned in an interrogation position wirelessly adjacent the plate. When in the interrogation position, the primary and secondary coils are inductively coupled, that is, form an inductive coupling, when the primary coil is energized at the resonant frequency. The plate includes at least one self-contained frangible continuity circuit electrically connected to the secondary coil. The inductive coupling induces an electrical current flow in the continuity circuit when the circuit is undamaged, and thereby provides the basis for a conclusion that the plate has a non-damaged status.

A detector cooperates with the primary and secondary coils when the interrogator is in the interrogation position. The detector detects the inductive coupling. An indicator cooperates with the detector to indicate the non-damaged status of the ceramic plate upon detection of the inductive coupling. The ceramic plate and the self contained continuity circuit do not contain and do not have mounted thereon, physical external electrical connectors which are external to the plate and electrically connected thereto.

The interrogator may further include a tuned resonant tank circuit which includes the primary coil. The resonant tank circuit has a characteristic property which has a first self-inductive value when the primary and secondary coils are not inductively coupled to each other, and wherein the inductive coupling is mutual induction. When the primary and secondary coils are inductively coupled, such that the electrical current flow is induced in the continuity circuit, the first inductive value property detectably shifts the resonant frequency of the tank circuit from the first self inductive value. For example the characteristic property may be resonant frequency, and the first self-inductive valve may be a first resonant frequency, in which case the resonant tank circuit has a resonant frequency at a first resonant frequency. The inductive coupling is mutually inductive such that the impedance and inductance of the secondary coil in the continuous frangible continuity circuit detectably shifts the resonant frequency from the first resonant frequency.

The detector advantageously includes a micro-processor to detect the shift of the resonant frequency. The detector may be mounted in the interrogator. The interrogator may include a primary drive circuit driving the primary coil within the tank circuit at the resonant frequency. The interrogator may be hand-held and the indicator may be mounted in the interrogator. The interrogator may be embedded in a tactical vest. The ceramic plate is mounted in the tactical vest.

In one embodiment a plurality of self-contained frangible continuity circuits are employed on the plate. In that case the secondary coil may include a plurality of secondary coils, where each secondary coil is electrically connected to only a corresponding the continuity circuit.

In a further embodiment the inductive coupling induces an electrical current flow in the continuity circuit when the circuit when the continuity circuit is undamaged, and the inductive coupling of the primary and secondary coils transfers the power via the secondary coil to the continuity circuit.

The detector and the indicator and an associated indicator circuit are mounted on the ceramic plate and are electrically connected to the secondary coil and the continuity circuit. The power is also transferred to the indicator circuit when the continuity circuit is undamaged thereby allowing the electrical current flow through the indicator circuit. A conditioning circuit may be electrically connected to the secondary coil, the detector and the continuity circuit.

Any or all of the secondary coil, the conditioning circuit, the detector, the continuity circuit may be mounted on the back surface of the plate opposite the front strike surface of the plate.

BRIEF DESCRIPTION OF THE DRAWINGS

In the drawings where similar reference characters denote corresponding parts in each view:

FIG. 4A is a diagram of plate integrity indicator circuit based upon mutual inductance that uses a passive continuous or closed conductive trace circuit and series connected secondary coil to magnetically couple with a powered primary inductive coil in an interrogator unit. When the primary coil circuit is energized with AC power, creating magnetic flux in the coil, the mutual inductance between the two coils and resultant resonant frequency of the tank circuit's primary inductive coil, which is influenced by the reflected impedance from the secondary coil, provides a 'good' plate signal on the interrogator unit.

FIG. 4B illustrates the system of FIG. 4A wherein the ceramic plate has a fracture which creates a crack or open circuit in the conductive trace and the series connected secondary coil. As a result the impedance of the secondary coil is negligible, and no inductive coupling is exhibited between the primary and secondary coil. The resonant frequency of the primary tank circuit in the interrogator is unchanged therefore registering a negative response indicating that the plate is damaged resulting in a negative plate integrity response. An LED indicator output on the interrogator unit provides indication to the operator that the plate is damaged.

FIG. 7a is a table of frequency, impedance and current measurements for an interrogator 145 KHz primary inductive coil tank circuit influenced by the mutual inductance of a ceramic plate secondary inductive coil.

FIGS. 10A-10C are three example configurations of a conductive trace, secondary coil and power conditioning and indicator board on the ceramic component of a hard armor plate for inspection of the plate using inductive power transfer, wherein: FIG. 10A is a ceramic plate with a single conductive trace and indicator sub-circuit powered by a single secondary coil; FIG. 10B is a ceramic plate with a single coil powering four conductive traces that each lead to their own indicator, allowing improved discrimination of the extent of any detected integrity problems; and, FIG. 10C is a ceramic plate with an alternative configuration where the plate has four discrete circuits each with their own secondary coil, indicator and sub-circuit, and conductive trace.

DETAILED DESCRIPTION OF EMBODIMENTS OF THE INVENTION

Figure 1:
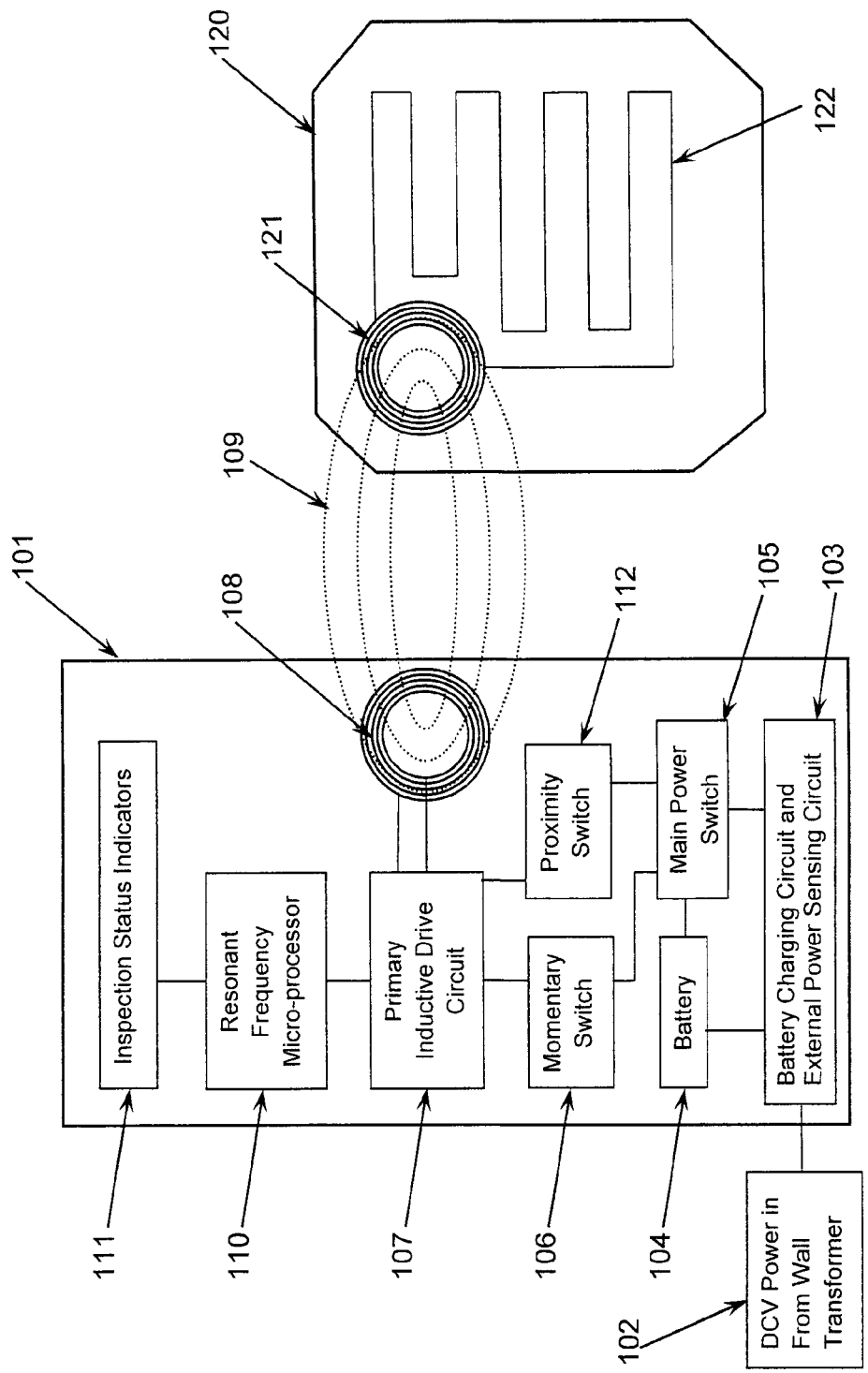
FIG. 1 is a schematic block diagram of a non-contact composite/ceramic hard armor inspection system for the rapid analysis of the ceramic components integrity using inductive techniques. Housed within an interrogator unit, a primary coil and drive circuit is inductively coupled by an alternating magnetic field to a secondary coil connected to a conductive trace and indicator output on the ceramic plate of hard armor plate.

Soft armor vests for both soldiers and tactical police usually are designed with large front and rear pockets into which hard armor plates can be inserted. Hard armor plates are the heaviest part of a personal or body armor system and can weigh as much as 4.5 kgs each. Significant research has been undertaken to reduce the weight of the plates whilst also improving the ballistic protective performance as the hard armor is one of the soldiers heaviest single weight burdens.

Hard armor plate construction falls into two principle groups; plates constructed with a ceramic strike face and adhered to a composite support backing, or plates that use no ceramic for the strike face and are made only of composite, such as an Ultra High Molecular Weight Plastic or a high tenacity fiber and resin.

For hard armor plates that employ a ceramic strike face, the ceramic is usually a sintered monolithic ceramic plate that is bonded to a backing of composite material. The strike face ceramic can also be a tiled matrix that is bonded to the backing composite material and then cut to shape. Typical ceramics used in conjunction with composite backing to form an armor system include: $Al_2O_3$ (Aluminum Oxide or Alumina); SiC (Silicon Carbide); $Si_3N_4$ (Silicon Nitride); and, $B_4C$ (Boron Carbide).

The ceramic may also be toughened or be performance enhanced with minor constituent additives such as Zirconia or carbon nano-tubes. In all, there is a multitude of ceramic permutations that can be used as a ballistic armor strike face material.

A variety of other materials may be added to the construction of the plates such as polycarbonate, thin layers of steel, carbon fibre, foams and various other materials that may provide an improvement to either ballistic performance or the plates ruggedness.

Hard armor plates come in different sizes to fit the user group and are designed to conform to body shapes using a simple single vertical curve, complex multi curve profiles, geometries with chamfered corners, edges and rifle cut outs. Plates may also be used in several locations on the body such as aforementioned chest and back plates, but also side and shoulder plates etc.

The present invention allows the ceramic body armor plate to be inspected while the plate remains inside the vest pocket, the user interface is improved, time for inspection is reduced to only a few seconds and the durability and reliability of the plate integrity components is increased. The invention provides an inductively coupled plate inspection system and procedure that allows the integrity of the ceramic component of a hard armor plate to be verified by a very simple, easy to interpret 'go/no go' in field inspection process that requires no physical connection or contact with the plate. The plate may be left within the pocket of the armored vest during the inspection.

A passive electronic damage detection circuit is self-contained upon the ceramic armor plate and does not require an external physical electrical connector or internal battery power to function. A continuity circuit is placed upon the ceramic plate that is electrically connected to an inductive coil allowing the ceramic plate to inductively couple to a coil within a handheld interrogator unit. The interrogator unit allows the operator to determine if the plate has been impacted, compromised or damaged sufficiently to produce hairline cracks within the ceramic component, such that the armor plate should be removed from service for more comprehensive inspection using for example x-ray.

Two implementations or embodiments are described herein. The first non-contact inspection implementation employs the varying characteristics of mutual induction between two co-located coils when one of the coils is magnetically energized. The second implementation provides non-contact electrical power inductively to a continuity and indicator circuit on the ceramic component of the hard armor plate.

The first implementation of a non-contact ceramic plate inspection system utilising inductive coupling is the application of circuits that detect characteristics of mutual induction between two coils when they are placed proximal to each other. When a plate is to be inspected, the handheld interrogator unit's embedded primary coil is positioned proximal to the secondary coil on the plate such that there is inductive or magnetic coupling between the respective coils. DC voltage provided by an internal battery in the interrogator unit or external source is applied to the interrogator's micro-processor controlled primary inductive driving circuit which provides a resonant AC power signal to the primary coil. The primary coil when located proximal to the secondary coil in the plate inductively couples via magnetic flux to the secondary coil. The primary drive circuit in the interrogator unit powers the primary coil at the self-resonant resonant frequency of the coils tank circuit. When the primary coil is in the proximity of a secondary inductive coil that is in a continuous or closed circuit, the mutual inductance created between the primary and secondary coil will affect the impedance and inductive value of the primary coil which in turn will change the resonant frequency of the primary coils tank circuit. The change in the resonant frequency of the primary coil or changes in other characteristic's of the resonant circuit is detected by a micro-processor in the primary drive circuit and an indication is provided to the operator. If the plate's conductive trace is a continuous circuit, the secondary coil on the plate will change the mutual inductance between the interrogator's primary coil and the plate's secondary coil and provide a positive indication of the plates integrity. If the ceramic plates conductive circuit is broken, the impedance and consequent mutual inductive coupling by the secondary coil will be negligible and will not change the resonant frequency of the primary coil tank circuit. In this case the micro-processor will provide a negative indication that the plate may be damaged and should be submitted for further inspection.

This feedback allows armor plates that would be difficult to access or be viewed by the soldier to be inspected without having to remove the plate from the vest. The magnetic field produced by inductive coupling can pass through materials that are non-conductive or non-magnetic. The inductive power can therefore be transmitted through the outer carrier fabric of garments, soft armor panels and the fabric, plastic and foam materials that may be used in the construction of a ceramic armor plate.

A further derivation could be the division of the plate into different sectors each with its own continuity circuit and secondary coil, allowing the extent of damage to be qualified. An inductive secondary coil could also be placed around the outside edge of the plate. The conductive trace may be screened directly on the plate or it can be printed on a delicate or frangible media. Conductive traces could be printed on both sides of the media to allow a more complex electronic circuit to be developed.

As the wireless inductive power can pass through the non-magnetic, non-conductive ceramic armor materials, this provides the opportunity to place the secondary inductive coil, secondary conditioning circuit and conductive traces on the back side of the ceramic plate. With the application of suitable adhesives the conductive trace could be broken if the composite backing is pulled away or separates from the back of the ceramic strike face. A separation between the ceramic and composite backing can cause a significant loss of ballistic performance for a ballistic plate and is known within the industry as a dis-bond. It can be demonstrated that there is a capability to detect both ceramic plate fracture or ceramic plate/composite backing dis-bond that is typical of damage found on ceramic armor plate. Inspection of the ceramic components of hard armor plates can be implemented at the most basic level of application or using a more sophisticated capability, all without physical contact using mutually inductive properties.

A second implementation includes a miniaturised interrogator primary circuit embedded within the tactical vest and connected to the soldiers' central computer. As an essential part of personal protection, the status of the armor plates integrity can be monitored without the attachment of wires or cables to the plate to ensure it has not been compromised.

The second implementation uses a plate integrity circuit that has incorporated into it an inductive secondary coil which receives non contact or wireless power from a primary inductive power coil in the handheld interrogating device. When a plate is to be inspected, the interrogators primary coil is positioned proximal to the secondary coil on the plate such that there is inductive or magnetic coupling between the respective coils and power can be transferred between them. DC voltage provided by an internal battery in the interrogator or external source is applied to the interrogator and powers the primary inductive driving circuit which provides a resonant AC power signal to the primary coil and its tank circuit. The primary coil when located proximal to the secondary coil in the plate inductively couples and transmits AC power via magnetic flux into the secondary coil. The AC power then transfers from the secondary coil through a secondary conditioning or rectification circuit and the conductive trace that is on the surface of the ceramic plate. If the conductive trace is continuous or closed, then power is provided to an indicating device integrated onto the conditioning circuit board and a positive response such as the lighting of an LED (Light Emitting Diode) on the indicator board is obtained. If the conductive trace is interrupted or open, then power is not provided to the indicating circuit or device and the LED remains non-responsive.

The inductive power can be transferred from the primary coil to the secondary coil over a distance that is determined by the circuit and coil design. A practical application distance would be a 1-3 cm stand-off distance for a handheld interrogator and up to 20 cm for a fixture mounted interrogator. The stand-off distance is principally determined by the diameter of the primary and secondary coils.

An example of a visual indicator would be the use of two or more LED's. The first LED can be used to indicate power is being received by the secondary coil, and that the second conductive trace coil should be indicating, removing any doubt the plate is receiving non-contact power. If the power LED lights and the integrity or conductive LED does not light then the plate must be removed from service for further inspection. If both LED's light then the plate can be left in service.

Alternately only a single LED could be used that only lights when power is available through the entire circuit, the secondary coil and the conductive trace.

A further derivation could be the division of the plate into different sectors each with its own continuity circuit and LED indicator so the extent of damage can be isolated. A coil could also be placed around the outside edge of the plate. All circuits would be powered from a single secondary coil, however an array of LED's would indicate which sector of the plate was damaged and/or how extensive the damage is.

A still further derivation could be the conductive trace is printed on a delicate or frangible media. Conductive traces could be printed on both sides to allow a more complex electronic circuit to be developed. The traces could include printing of the secondary coil, conductive plate integrity traces as well as any sub-circuit PCB traces that may be required for the attachment of electronic components such as but not limited too resistors, capacitors, integrated circuits, indicators or sensors etc. The printed traces may include circuits or elements of RFID circuits such as antennas or transceiver circuits that provide feedback to a primary RFID data analyser.

A RFID antenna could be placed onto the plate with a RFID IC that would allow communication with the interrogator after receiving inductive power from the interrogator unit.

The connection or PCB to which the LEDs are connected would be very thin or printed on a flexible film substrate such as Mylar™ or Kapton™ as the circuit board derives mechanical support from the ceramic plate. This would allow it to be placed anywhere on the front or sides of the armor plate. As most plates have a fabric cover, matching holes can be constructed in the cover to allow the LED to be seen, or alternatively sufficiently bright LED can be used so that they shine through the fabric without the need for holes. This would provide the ultimate in protection to the conductive trace as it would be sandwiched between the back of the ceramic plate and the composite backing.

As with the mutual inductive implementation, with the application of suitable adhesives, the conductive trace could be broken if the composite backing is pulled away or separates from the back of the ceramic strike face. As stated above, this situation also causes a significant loss of ballistic performance for a ballistic plate and is known within the industry as a dis-bond. It can be demonstrated that there is a capability to detect to both ceramic plate fracture or ceramic strike face/composite backing dis-bond that is typical of damage found on ceramic armor plate. Inspection of ceramic components of the hard armor can be implemented at the most basic level of application or using a more sophisticated capability, all without physical contact using inductively transmitted power.

If a hard cover and impact absorbing foam is placed on the front of the plate, the LED array can be placed on the side or top edge of the plate. Regardless of the plate design or cover materials, accommodations can be made so the LED or LED array or other indicator can be observed.

Other feedback mechanisms are possible. Non visual indicators, for example an audio or vibratory device introduce the possibility of inspecting the plate when it is inside a vest and not having look at or remove the plate from within the pocket. An audio or vibratory device could be used in place of the LED, which emits an acoustic or lower frequency output when energized. Such devices can be extremely thin and easily incorporated into the packaging of the plate.

Both the primary and secondary inductive circuits and coils are protected from the elements by, respectively, either the interrogator housing or the cover of the hard armor plate. The primary and secondary inductive coils in both the mutually inductive and inductive power transfer implementations will work in any environment including being fully submerged and are unaffected by and will operate in environmental conditions such as rain, mud and snow, and will also function in the presence of dust, sand, dirt, moisture, submersion and POL's, that is in the presence of conditions of conditions which are detrimental to standard or MILSPEC connectors that are required by other armor test techniques.

Mutual coupling between two coils exist, when one coil is in the magnetic field created by the other coil. Consider two magnetically coupled coils: When an alternating current flows in the primary coil, then an alternating magnetic flux is produced in the same coil. Part of the magnetic flux produced can couple or link with a second coil placed within proximity to the primary coil. Since this flux will also be alternating, an induced current will be produced in the second coil without physical contact between the coils.

Two coils are magnetically coupled when an alternating current is passed through one of the coils. When one of the coils is in a tuned circuit (i.e. the primary tank circuit) the electrical characteristics of the tuned circuit are affected by the mutual inductance between the coils as the EMF generated in the secondary coil by the primary coil in turn effects the properties of the primary coil due to reflected impedance from the secondary coil. The mutual inductance between the coils however depends only on the geometrical properties of the two coils such as the number of turns and the radii of the two coils and is independent of the current in the coils.

The coupling constant is independent of the number of turns in a coil. The number of turns in a coil determines the magnetic field which will be produced for a given current. The coupling constant is concerned with how the lines of magnetic force produced by one coil interact with another coil, and hence the coupling constant between two air spaced coils depends only on their physical size and separation distance and relative orientation. Hence to obtain optimal coupling between primary and secondary coils in an air-cored transformer we can change the size and spatial relationships of the coils, or employ a ferrite backing to optimise the inductive coupling and the wireless power transfer efficiency.

A series of tests were conducted between a tank circuit with a 10 turn primary coil influenced by the mutual inductance of a 40 turn secondary coil placed at distances from 1-15 mm. The 10 turn coil had an inner diameter of 22 mm, an outer diameter ("OD") of 35 mm, an inductance of 1.241-05 H, impedance Z of 12.985Ω and was coupled in parallel with a capacitor of 9.88-08 F to produce a calculated primary resonant frequency of 143.7 KHz, with an actual resonant frequency of 145.6 KHz obtained. The secondary coil had an inside diameter of 20 mm, outside diameter of 35 mm and an inductance of 1.03-05H and was a placed in a closed or continuous circuit. Principle data from the tests is presented in FIG. 7a. Plots of impedance, inductance and current versus frequency are provided in FIGS. 7-9.

At a separation distance of 15 mm, the mean radius of the coils, the reduction in mutual induction between the two coils changes the primary tank circuit resonance by only 2% or 2-2.5 KHz. As the difference in resonant frequency should preferably be greater than 10 KHz for reasonable differentiation by the micro-processor, the inspection distance for the 35 mm diameter coils must be kept to less than 6.0 mm. To increase the inspection distance stand-off, the diameter of the coils can be increased, as the separation distance between the coils at which useful magnetic coupling occurs increases proportionally. Therefore if a useable interrogation distance of 0.5-1.5 cm is desired, the OD of the coils must be approximately 7.0 cm. For sue in an armor plate, there is actually no reasonable technical limit for the maximum coil diameter other than the size of the plate and the size of the primary coil head on the interrogator making it unwieldy to use. Alternately or in conjunction with a coil diameter increase, the resonant frequency of the tank circuit can be increased. For example, if we take two coils with a 30 mm diameter and a primary tank circuit resonant frequency of 720 KHz, at 10 mm of separation between the primary and secondary coils the resonant frequency of the primary tank circuit is 747 KHz. If we go to a higher primary frequency of 1,786 KHz, now at 15.0 mm of separation between the primary and secondary coils the resonant frequency of the primary tank circuit is 1,843 KHz, which is easily differentiated by the micro-processor from the primary tank circuit resonant frequency. As the thickness of the outer fabric covering is 0.5 mm, and, if present, a polycarbonate covering is 1 mm, there will be no difficulty in optimizing a coil diameter that allows a mutual inductance based inspection technique to be implemented.

For the inductive power transfer implementation, one of many iterations of an inductively powered continuity integrity circuit is a series circuit comprised of a secondary coil to receive inductive power from a non contacting primary coil, a single trace conductive loop printed onto a ceramic plate and an indicator device such as an LED, acoustic emitter or otherwise. To provide a robust circuit to power the indicator, minimal additional support electronics such as a rectifying diode and a current limiting resistor are required. All these components are extremely low profile (<0.5 mm) and would not be noticeable under the fabric cover of an armor plate. The secondary coil and continuity circuit can be placed either on the strike face or back side of the ceramic plate with the indicator sub-circuit positioned anywhere on the plate including the front, back or perimeter edge. As the ceramic circuit does not depend on the measurement of resistance, but the low power flow of electricity, the circuit has little sensitivity to trace resistance. The system allows the plate to be inspected without connectors or cables, or the removal of the plate from its pocket in a vest, and may be done as frequently as is required to assure the user of the plate integrity, and within less than five seconds per inspection. The circuit is insensitive to manufacturing tolerance and provides positive and negative plate integrity indication only by virtue of circuit continuity.

In use, an interrogator unit that has within it a powered primary inductive coil would be used to generate a magnetic flux that inductively connects to the secondary coil providing power to the continuity circuit. If the ceramic plate has no cracks the circuit will be continuous and the indicator board will receive power, if the plate has one or more hairline cracks the circuit will not be continuous and the indicator will not receive power. If a 'no go' indication is provided, the plate can then be removed for more detailed inspection.

A quick, efficient and convenient arrangement for the indicator would be to have an LED or LED array on the top edge of the plate. The plate pocket flap of the carrier garment would be opened to expose the top of the plate. When the interrogator is brought into proximity of the secondary coil and is activated, the response of the indicator LED is easily seen without having to remove the plate from its pocket.

For both the mutually inductive and inductive power transfer implementations, the conductive loop trace must have matching tensile characteristic to the ceramic such that it will crack with the ceramic. Such conductive materials may be inks, foils or other conductive materials that will crack when rigidly bonded to a ceramic plate. Conductive ink may also be placed on a carrier material or media such as a pre-printed paper or other frangible media which would then be adhered to the ceramic surface. Further design and engineering options are conductive inks available with different elasticity. A more elastic versus brittle ink may be applied so that micro-surface cracks in the plate do not break the conductive circuit and create a false positive for damage reading.

The secondary inductive coil can be of many geometries and sizes but performs best when it is sized to match the size and geometry of the primary coil in the interrogator. The most favourable geometry of the coil is one that is low profile or flat so that it conforms to the plate and does not change the surface profile of the plate. The most typical geometry would therefore be planar with a rectangular, circular, triangular any other flat regular or irregular geometric shape. It is also possible for the coil to have a low profile cylindrical shape, however these shapes would generally not be suitable for the intended application. For a 1-3 cm standoff between the plate and the interrogator unit, the primary and secondary coil would have a diameter of 4-9 cm. The inductive coupling is proportional to the diameter of the coils with the useable separation distance range for inductive power coupling or mutual inductance characterisation being the mean radius of the coils. For greater stand-off distance the diameter of the coils would therefore be increased, with the practical limit being the outer dimensions of the plate. The secondary coil can be configured as an air backed coil or if required, its power transfer efficiency can be enhanced by using a thin planar ferrite backing. The ferrite element can also be of multiple material types and would be chosen to match the resonant frequency of the primary inductive system.

The secondary coil may be made of wire, be a printed trace on fibreglass board, Mylar™, Kapton™ or other substrates suitable for electronic circuits. It may be placed over the conductive trace as long as they are electrically isolated. This allows the conductive trace to cover an area as large as possible and provide inspection for the most surface area of the plate.

A proximity sensing system may be built into the primary circuit so that the operator knows that he has placed the interrogator close enough to the plate that magnetic coupling to the secondary coil can be established. An example proximity sensor would be a hall effect sensor on the interrogator that is triggered by a small magnet placed at the center of the secondary coil.

The plate interrogator can either be a hand held or fixture mounted device. It is used to analyse mutual inductance properties or provide power inductively to the secondary coil and plate integrity circuit embedded upon a ceramic armor plate. The interrogator unit for either inductive inspection application has many common attributes.

The interrogator can either be battery powered, or powered via a low voltage wall transformer. A DC voltage is applied to the inductive drive circuit which can be any of multiple designs that perform this function. Typically, but not limited to, the circuit uses an oscillator that determines the frequency at which the inductive circuit will resonate, that feeds into a half or full bridge driver. The output of the driver is connected to an inductive coil and a capacitor which comprise a resonant tank circuit. The inductance value of the coil and the capacitive value of the capacitor are chosen so that a resonant tank circuit of higher voltage than the drive voltage is created when the drive voltage is applied to it. The interrogator system described and its tank circuit can be designed to operate at any resonant frequency however typical frequencies for low power inductive power transfer are the low frequency range of 100-500 KHz, and a high frequency centered around 13.56 MHz range, such as used for RFID devices.

Example additional sub circuits that could be included in the driver are, voltage regulation, frequency feedback circuit to optimise power out, over temperature and over current protection circuits, timed interval driver power on, and sleep circuits to shut down the device when it is not used for a period of time.

When the interrogator unit is used for mutual inductance analysis, it must be able to identify resonant frequencies of the primary coil and then provide qualified feedback to the user. There are many methods using both hardware and software solutions to determine resonant frequency as would be known to one skilled in the art. One method that can be employed is that the primary coil frequency can be swept using a voltage controlled oscillator (VCO) that feeds a full or half bridge driver which in turn is connected to the coil tank circuit. Alternately, an output of a microprocessor takes the place of the VCO and the control logic turns the bridge driver on and off. As the frequency is swept, the coil current may be tracked by the micro-processor using zero-crossing detection via a shunt resistor or it may track peak voltage. The microprocessor sweeps the frequency up and down and looks for the peak voltage to obtain the frequency at or very near resonance. Many microprocessors have a digital/analog output which can perform this control function. The more peaked the frequency response the easy it is to discriminate the resonant frequency.

In use, a powered-on interrogator unit is brought up to the hard armor plate. The proximity sensor in the center of the primary coil is triggered when the unit is within the correct distance and centered over the secondary coil on the plate. Once the proximity sensor is triggered, the primary coil driver is turned on and the micro-processor performs a frequency sweep. If the plate circuit is closed i.e. the plate is good, then the mutual inductance created by the secondary coil and its closed circuit change the resonant frequency of the primary coil so that it falls within a specified frequency range that identifies it as a good plate by the interrogator unit. If the secondary coil circuit is open, then the primary coil resonates at its fundamental resonant frequency and the plate is determined to have failed the inspection.

The packaging of the interrogator can take many forms, from a simple box to a handheld pendent style package or other ergonomic shapes. The interrogator housing would typically be constructed from plastic such as ABS or PVC or any other non-magnetic, non-conductive material that does not impede the transmission of the inductive magnetic flux. The housing may include a corner or edge guide that mechanically helps with positioning of the interrogator over a specified location on the ceramic plate. This would provide optimal coupling and power transfer between the two inductively coupled coils. The primary coil assembly may have any orientation. It may be placed either parallel to the plate to be inspected, be perpendicular to the plate or be placed on a swivelling head so the operator can determine what angle it is to be used at.

Various audio indicators or visual displays can be placed on the interrogator to provide the operator with feedback of battery power level, main power circuit activation and the response to the inspection of an armor plate if a mutual induction process is utilised. A main power switch provides power to the sleep circuit, a second switch is then pressed to activate the primary coil driver circuit if a proximity detection circuit is not employed.

DETAILED DESCRIPTION WITH REFERENCE TO THE DRAWINGS

With specific reference to the drawings wherein like reference numerals denote corresponding parts in each view, the implementation of an economical non-contact or wireless ceramic body armor inspection system suitable for use in the battlefield by non-specialized operators, must be rugged and easy to support. A schematic block diagram of such a system is presented in FIG. 1. An interrogator unit (101) which may be handheld or mounted to a fixture contains within it the required drive circuit electronics to power a primary inductive coil (108). The unit is powered by either its internal rechargeable battery (104) or externally by power from a DCV wall transformer (102) that can power the interrogator directly and recharge the battery through a battery charging external power sensing circuit (103). DC power is provided to the main inductive drive board (107) through a main power switch (105) and a momentary power switch (106), which would be pressed when power is to be provided to the inductive drive circuit (107). Optionally the drive circuit can have incorporated into it a proximity switch (112) such as hall-effect sensor that detects when the interrogator is sufficiently close to a plate for the plates coil to be inductively powered. The inductive drive circuit is of conventional design and utilises an oscillator and tuning sub-circuits that provides a signal to a half or full bridge driver connected to a tank circuit comprised of the primary inductive coil and a capacitor. The interrogator system described and its tank circuit can be designed to operate at any resonant frequency however, as stated above, typical frequencies for low power inductive power transfer are the low frequency range of 100-500 KHz, and a high frequency centered around 13.56 MHz range, such as used for RFID devices. When used for mutually inductive ceramic plate analysis, a microprocessor (110) in the primary drive circuit allows for a frequency sweep function for resonant frequency detection of the primary coil tank circuit. The operator of the interrogator unit is informed of the status of the plate inspected by either audio or visual indicators such as a speaker or an LED via an indicator board (111) that is provided with outputs form the micro-processor circuit.

The alternating current provided to the primary inductive coil (108) produces an alternating magnetic field (109) which allows the interrogator unit to inductively couple with the secondary coil (121) that is integrated onto the ceramic component (120) of the hard armor plate. The secondary coil (121) is connected to a conductive trace circuit (122) that in one embodiment is silk screened directly onto the plate or has been printed onto a frangible media and adhered to the plate. The secondary coil (121) and conductive trace (122) form a closed circuit that develops impedance in the secondary coil (121) such that it affects the mutual inductance of the secondary (121) and primary (108) coils when they are placed in proximity. By coupling to the plate inductively, the need for connectors is eliminated and inspection of the plate is greatly facilitated as it can now be left within the plate pocket of the protective vest. Further the function of the inspection circuit is enhanced as there are no cable or connector interfaces to fail.

Figure 2:
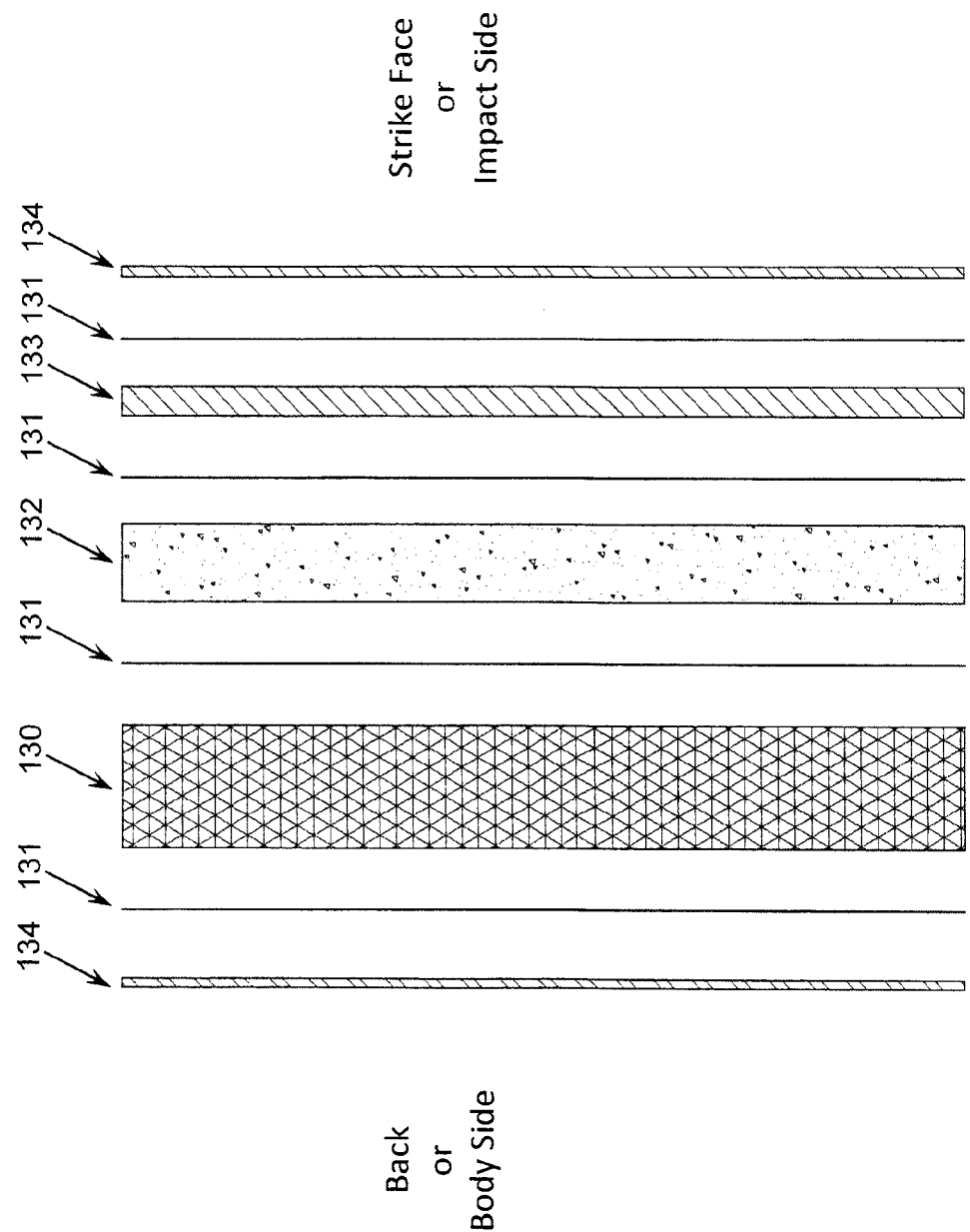
FIG. 2 is an exploded sectional diagram of the representative components of a hard armor composite/ceramic plate.

An exploded cross-sectional view of the component layers that comprise a hard body armor plate is seen in FIG. 2. The two principle components of the hard armor plate are the composite backing (130) and the ceramic plate (132) which are bonded with a bonding layer (131). A shock attenuating layer (133) of foam or polycarbonate to make the plate less susceptible to general use impact damage may be placed on the strike face of the armor system, however this layer is not always found within a plate design. The plate assembly is then covered with a bonded outer layer of durable nylon cloth or plastic (134). The inductive coil, and conductive trace can be placed on either the back side or the strike face of the ceramic as the magnetic field can penetrate all non-magnetic, non-conductive materials used in the construction of the plate including the ceramic itself.

Figure 3B:
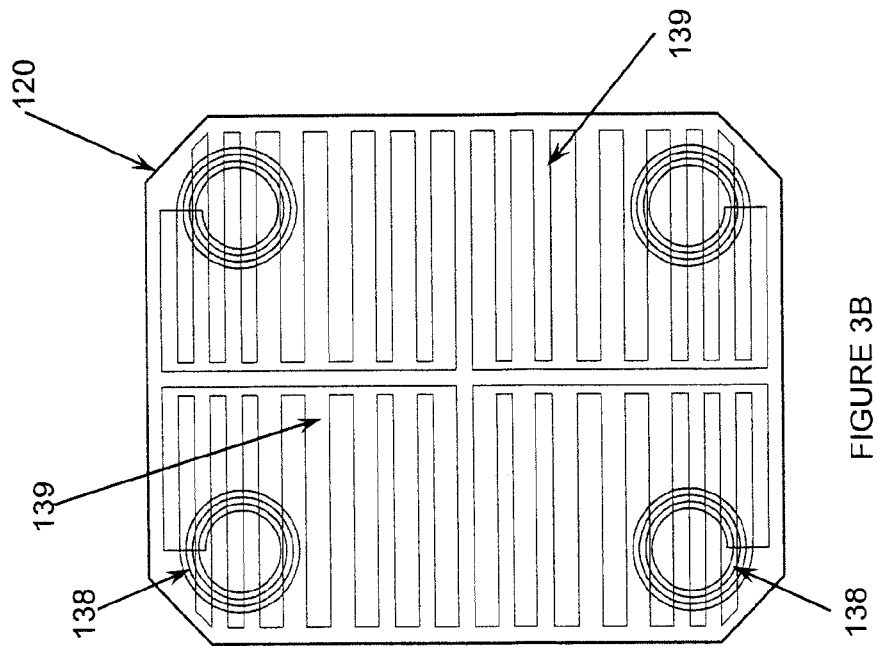
FIG. 3B is a ceramic plate with an alternative configuration where the plate has four discrete circuits each with their own secondary coil and conductive trace.
Figure 3A:
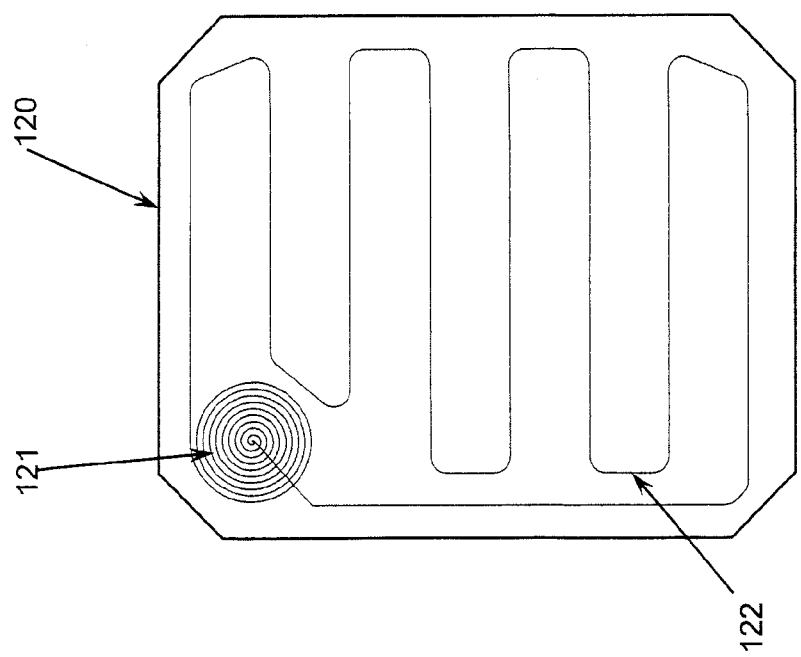
FIG. 3A is a ceramic plate with a series circuit comprised of a single conductive trace and a single secondary coil.

For interrogators units configured for plate inspection using mutual inductive coil properties, the design of the conductive trace as shown in FIGS. 3A and 3B or variants thereof. Optionally it may be desirable to modify the inductive response of the plate circuit and make it a tuned circuit. This may be accomplished by the addition of components such as capacitors connected either in series or parallel with the coil. FIG. 3A illustrates that the ceramic (120) component of the hard armor plate needs only be provided with a secondary coil (121) and conductive trace (122) to be inspected as an untuned circuit. For greater inspection fidelity, FIG. 3B illustrates that a quadrant conductive trace pattern (139) can be applied with a secondary coil (138) in each quadrant providing the required inductive coupling.

In FIG. 4, the integrity of the ceramic (120) is determined by the continuity of the conductive trace (122) in conjunction with the mutual inductance of the secondary coil (121) that is a part of a closed conductive trace circuit (122). FIG. 4A illustrates that when a plate is inspected using mutual inductance (109), the feedback on the status of the plate (120) is provided to the user by the interrogator unit (101). There are several ways of indicating the status of a ceramic component, two are shown in FIG. 4A. One indicator may be an audio indicator or small chirp speaker (142). The other may be a visual indication such as an LED (141). For example when the indicator sounds or lights, the ceramic plate being tested has passed. FIG. 4B illustrates that when the ceramic (120) is fractured (144) and the conductive trace (143) is now open as a result of the breaks in the trace (145) that when the interrogator unit (101) attempts to inductively couple (146) with the secondary coil (121), there is insufficient reflected impedance from the secondary coil (121) as a result of it being in an open circuit. There is no change to the self-resonant frequency of the primary coil tank circuit, indicating a failure of the trace and hence the ceramic (120). In general, it is not prudent to not provide feedback if a ceramic does not pass a test, therefore a fail LED indicator (147) of different colour may be used instead to inform the user the ceramic has failed the test.

Figure 5:
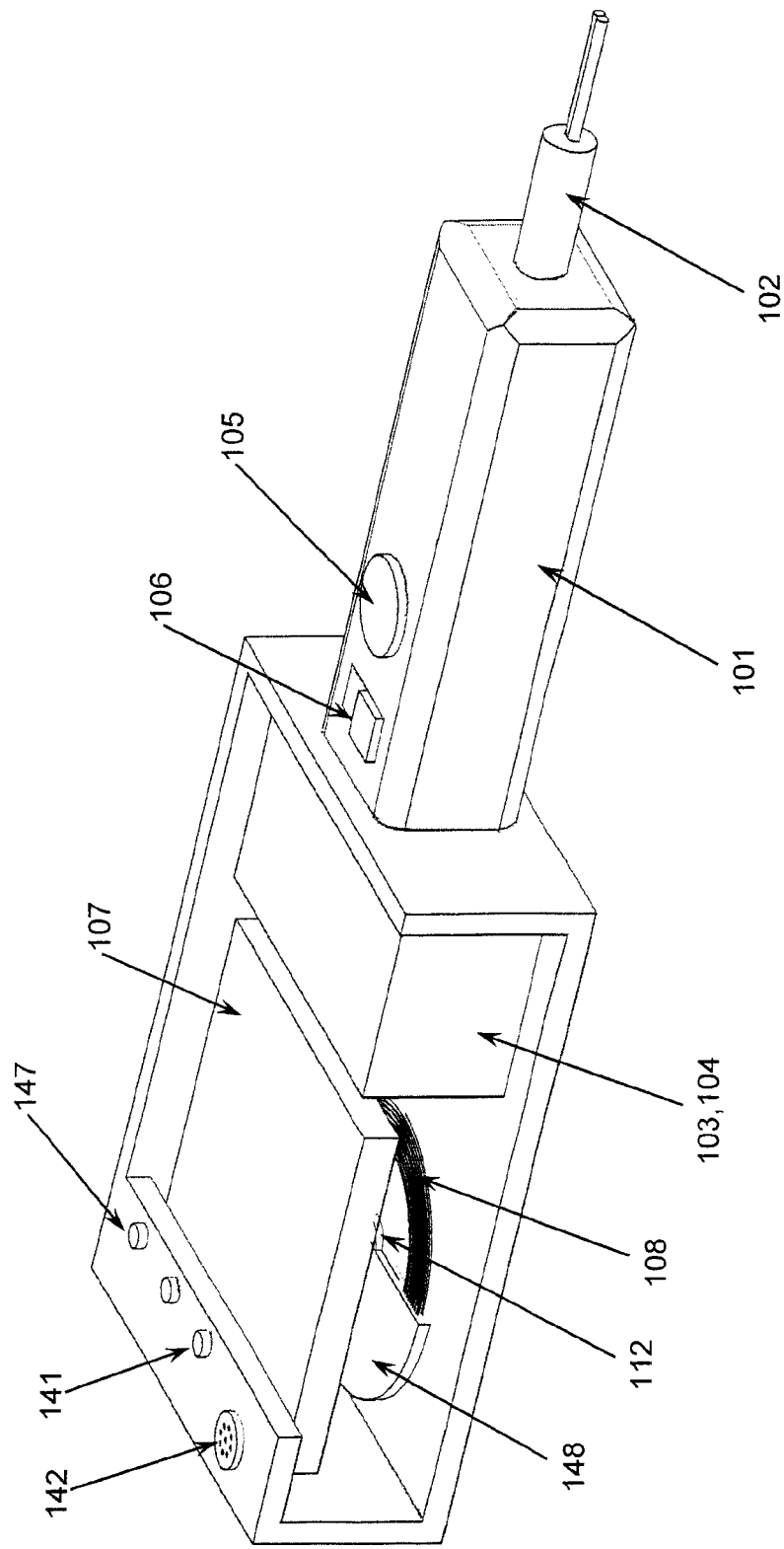
FIG. 5 is a partially cutaway perspective view illustration of a hand held interrogator unit with optional DC power input. In this view the primary inductive coil is parallel to the main surface of the plate to be inspected.

FIG. 5 is an cutaway illustration of handheld interrogator (101) configuration. The housing of the interrogator could be made from plastic as this allows the magnetic field of inductive energy to pass through it. DCV power can be provided to the hand unit by an external source (102) that can provide power and charge the internal battery (104) at the same time through the battery charging circuit (103). The main inductive drive circuit and frequency sweep micro-processor (107) provides the AC power signal to the planar primary inductive coil (108). To provide greater magnetic coupling to the ceramics secondary coil, the primary coil can be provided with a ferrite backing (148). If a proximity sensor (112) were to be used to activate the main drive circuit, instead of the momentary power switch (106), then it would be located at the center of the primary coil (108) and would be activated for example by a thin magnet placed within the center of the secondary coil. The interrogator unit primary drive circuit would then be automatically turned on only when it was within the desired range and located axially over the secondary coil. Indicator LED's can be provided to inform the user of the status of the interrogator unit for such requirements as power on, primary coil energized, plate sense, low battery etc. If the interrogator unit has been configured to inspect a plate using mutual inductance, the plate integrity status is provided to the user by the interrogator unit with an audio signal emitted by an annunciator (142) or visually by a LED indicator (141,147).

Figure 6:
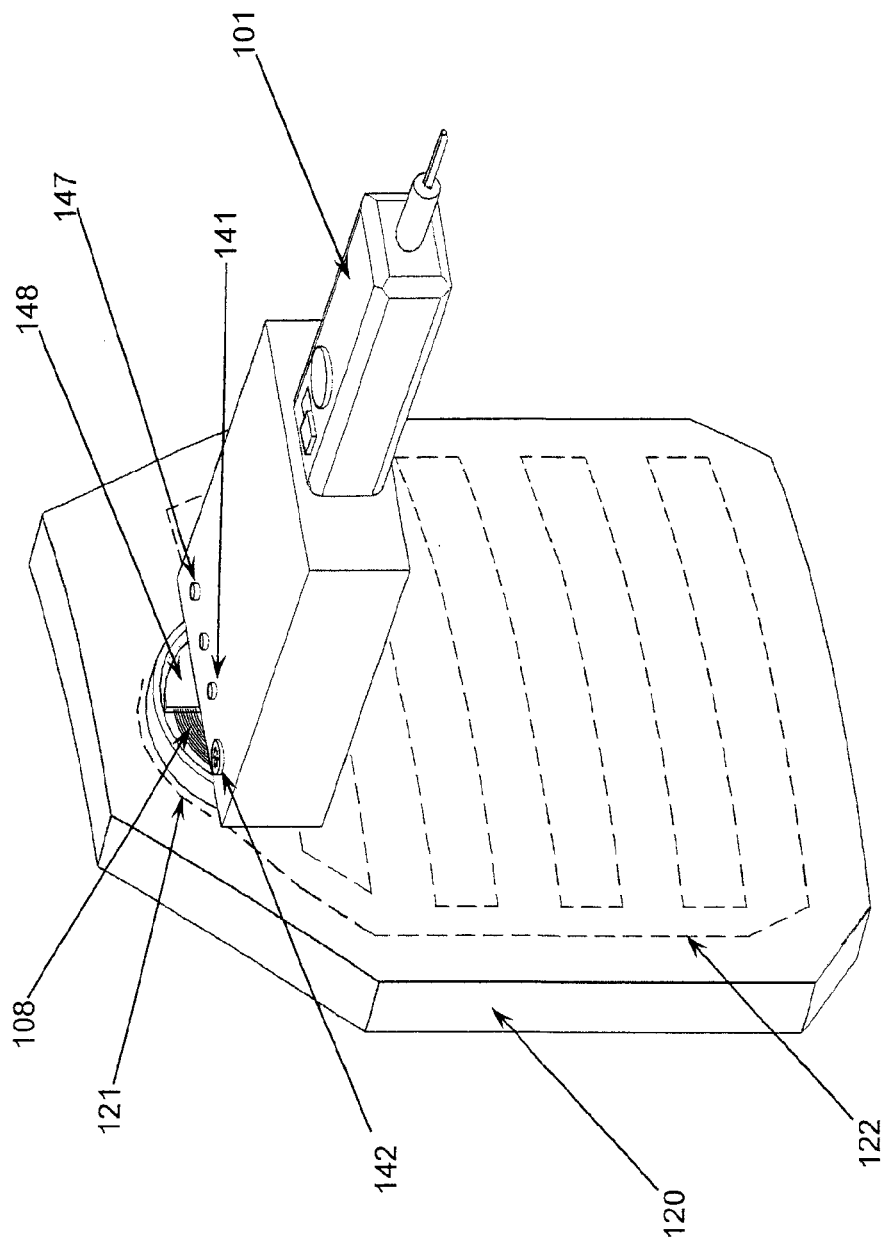
FIG. 6 is an illustration of the interrogator unit of FIG. 5 positioned 1-2 cm away from the surface of the hard armor plate with the primary inductive coil assembly oriented perpendicular to the surface of the plate. Mutual inductance between the interrogator unit and the plate allows the operator to determine if the ceramic component of the plate has been damaged.

FIG. 6 illustrates an interrogator unit (101) being used to test a ceramic component (120) of a hard armor plate (shown without an outer cover) using mutual inductance between the primary coil (108) and ferrite backing (148) that are shown perpendicular to the plate surface and located proximally to the ceramic's secondary coil (121).

Figure 7:
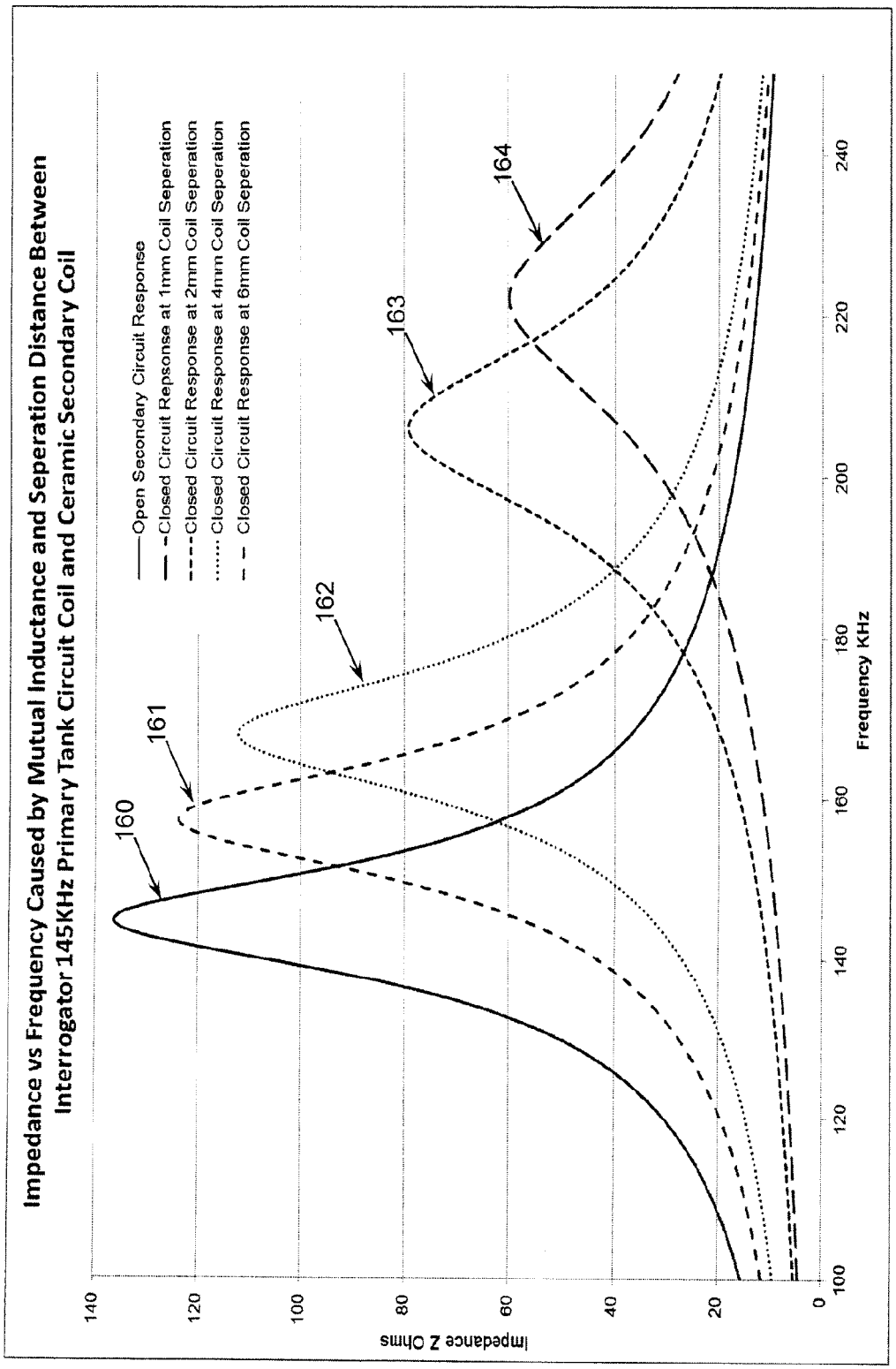
FIG. 7 is an impedance analyser data plot of impedance versus frequency for the 145 KHz primary tank circuit coil of the interrogator unit. The resonant frequency and impedance of the circuit is affected by the proximity and inductive coupling or mutual inductance between the primary coil and the secondary coil on the ceramic component of the hard armor plate. As the separation distance between the primary and secondary coil varies, the magnetic coupling and the mutual inductance also changes, affecting the resonant frequency of the primary coil tank circuit.

A plot of the change in impedance of the 145 KHz primary tank circuit coil of the interrogator unit versus resonant frequency as caused by the effect of the mutual inductance and coupling between the primary and secondary coils is provided in FIG. 7. The primary coil which is a part of tuned circuit and the amount of mutual inductance between the two coils determines the shape of the frequency response curve. Although no boundaries are defined, the two coils go from loosely coupled to more tightly coupled as they are brought more closely together. The highest primary tank circuit impedance (160) is obtained when the primary coil resonates by itself without any influence from a secondary coil. This response curve (160) peaking at 145 KHz, and with a relatively high Q or Quality Factor, is also the response that is obtained by the interrogator unit when the conductive trace and secondary coil circuit on the ceramic is open or broken as the result of fracture in the ceramic. For a ceramic plate that has good integrity, the conductive trace and secondary coil circuit trace are closed. When the two coils are 6 mm apart (161) and are loosely coupled, with the primary tank circuit resonant frequency peaking at 157 KHz, the impedance response or frequency bandwidth still remains narrow with a high Q which allows good selectivity. This can also be seen in the frequency response of the coil at 4 mm (162) of separation, as the shape of the response or Q is still relatively high. As the coils become closer together the coupling and the amount of mutual inductance increases, the bandwidth of the response grows and the Q is reduced as the slope of the curves becomes less steep. At the same time however, the peak frequency of the primary tank circuit has moved rapidly away from its self-resonance frequency due to the increased change in impedance created in the primary tank circuit, thus still allowing for easy identification of the resonant frequency. At 2 mm of separation (163) the resonant frequency is now 206 KHz and at 1 mm (164) the resonant frequency is 222 KHz. From these response curves it can clearly been seen how the effect of mutual inductance can be used to discriminate the status of the ceramic's conductive circuit and therefore the plate integrity.

Figure 8:
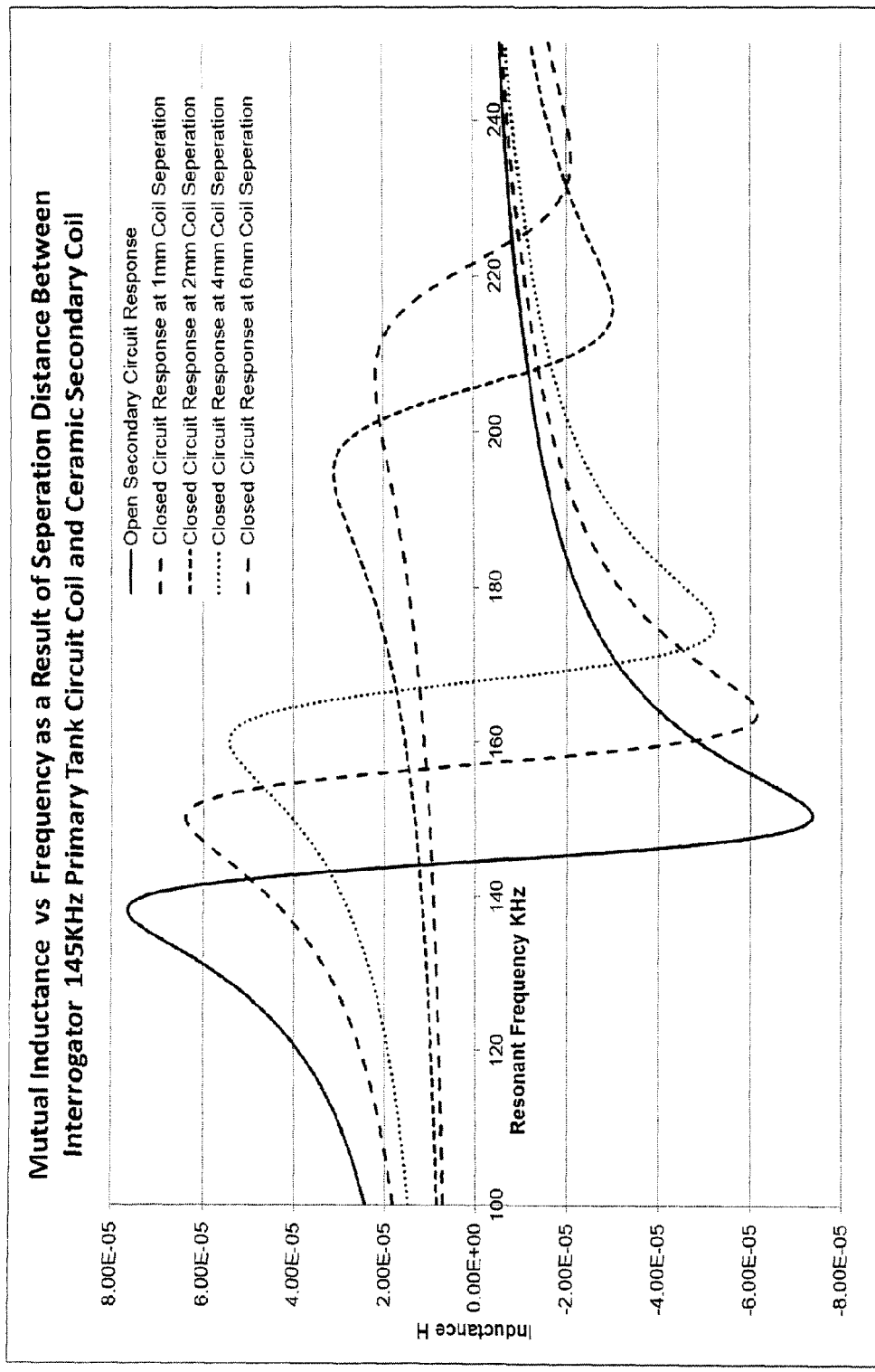
FIG. 8 is an impedance analyser data plot of the mutual inductance versus frequency for the interrogator 145 KHz primary tank circuit coil of FIG. 7.
Figure 9:
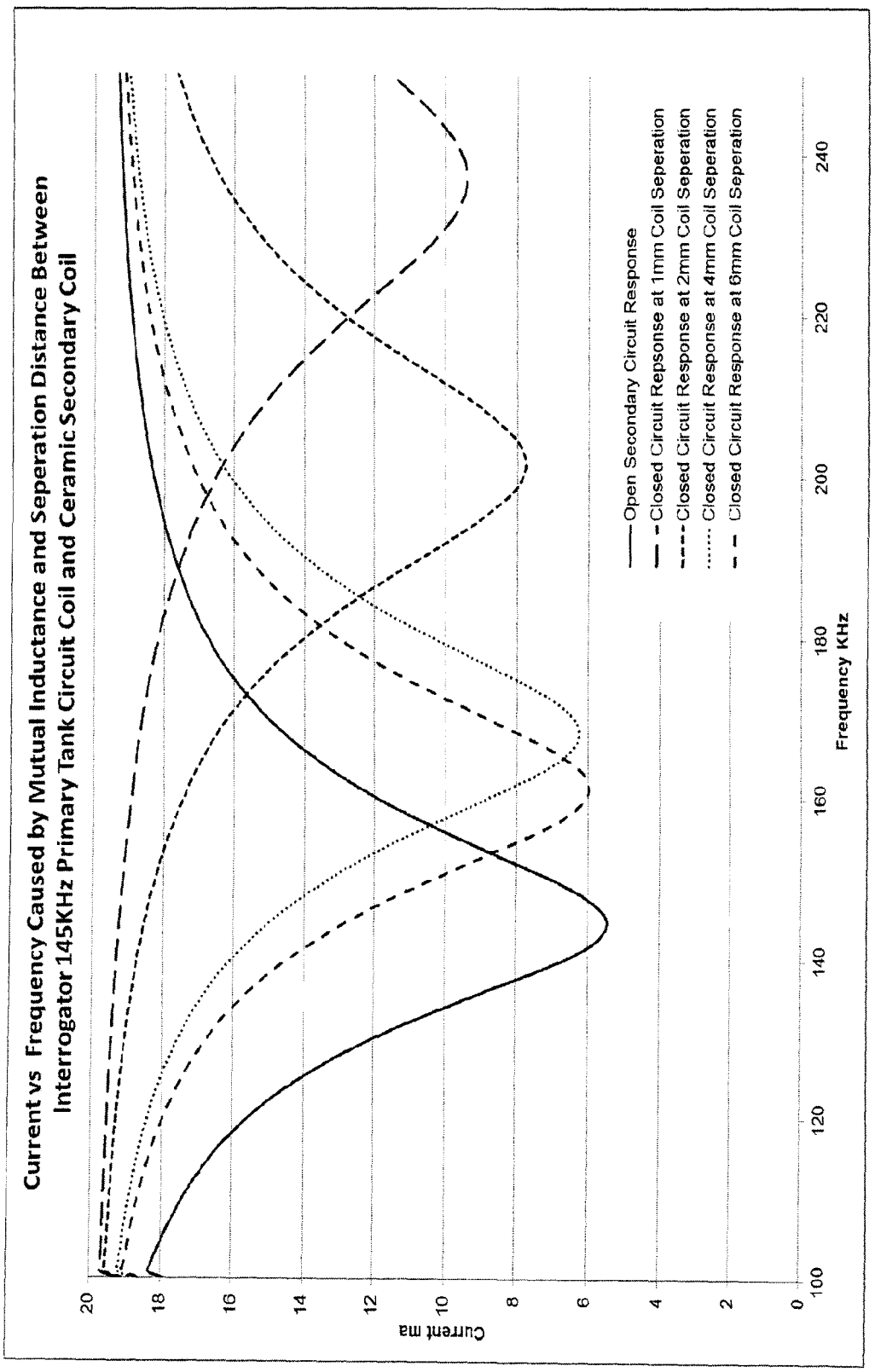
FIG. 9 is an impedance analyser data plot of the tank circuit current versus frequency for the interrogator 145 KHz primary tank circuit coil of FIG. 7.

FIG. 8 is a plot of the inductance of the primary coil versus frequency for the 145 KHz primary tank circuit coil of the interrogator unit as caused by the effect of the mutual inductance and coupling between the primary and secondary coils. The inductance value of the circuit crosses through zero at each of the resonant frequencies described in FIG. 7. FIG. 9 is a plot of current for the same coil tests conducted in FIG. 7, showing the current through the tank circuit goes to a minimum value at resonance.

Figure 10:
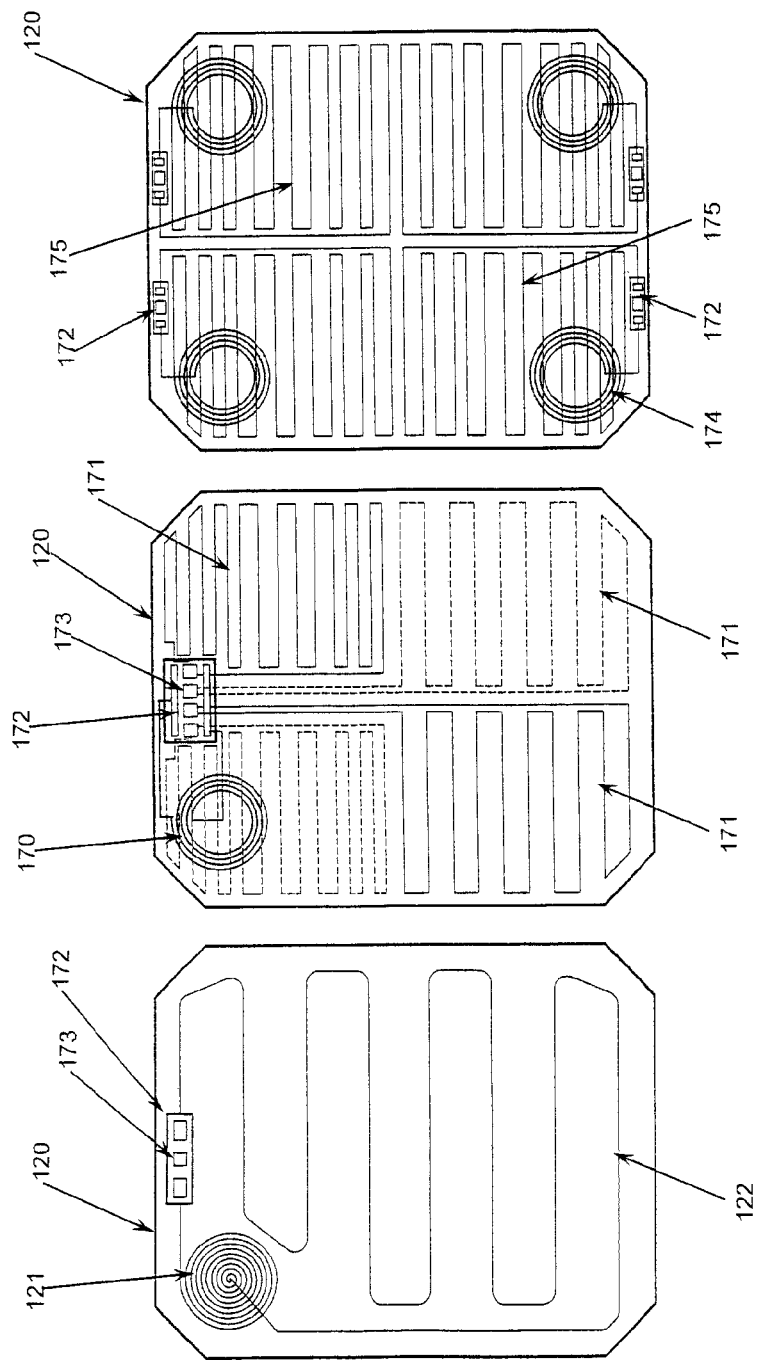

FIG. 10 provides an illustration of three alternate configurations of secondary coil and conductive trace incorporating an on-plate indicator board that is provided with power inductively through the secondary coil and conductive trace. FIG. 10A shows a basic plate integrity configuration comprised of a ceramic plate (120), secondary inductive coil (121), conductive trace (122) and power conditioner/indicator circuit (172) with LED indicators (173). When the conductive trace (122) on the ceramic plate is continuous, representing a plate that has integrity, inductive AC power received by the secondary coil (121) is rectified and regulated by the power conditioning board (172) and power is provided to an LED indicator light (173). The indicator circuit (172) can be placed on an edge of the plate, such as the top edge when a shock attenuating layer is used on the plate that may prevent the indicator from being observed when the circuit is energized. The indicator circuit can be constructed such that it has a very low profile of less than 0.5 mm by using micro flexible circuit substrates such as Kapton™ or Pyralux™ and low profile electronic components. A single path conductive trace can be made into any pattern, simple or complex as is limited only by printing process and cost. For increased spatial resolution the trace can be split into any number of separate integrity circuits. FIG. 10B shows a plate that has a conductive trace (171) in each of the four ceramic quadrants that are all powered by a single coil (170) via a power conditioning and indicator board (172) with an indicator LED (173) for each of the four quadrants. This trace configuration allows a user inspecting the plate to obtain greater fidelity in identifying the extent or location of damage to a plate. A further iteration is presented in FIG. 10C where each of the quadrant traces (175) has its own inductive power coil (174) and power conditioning indicator board (172).

Figure 11:
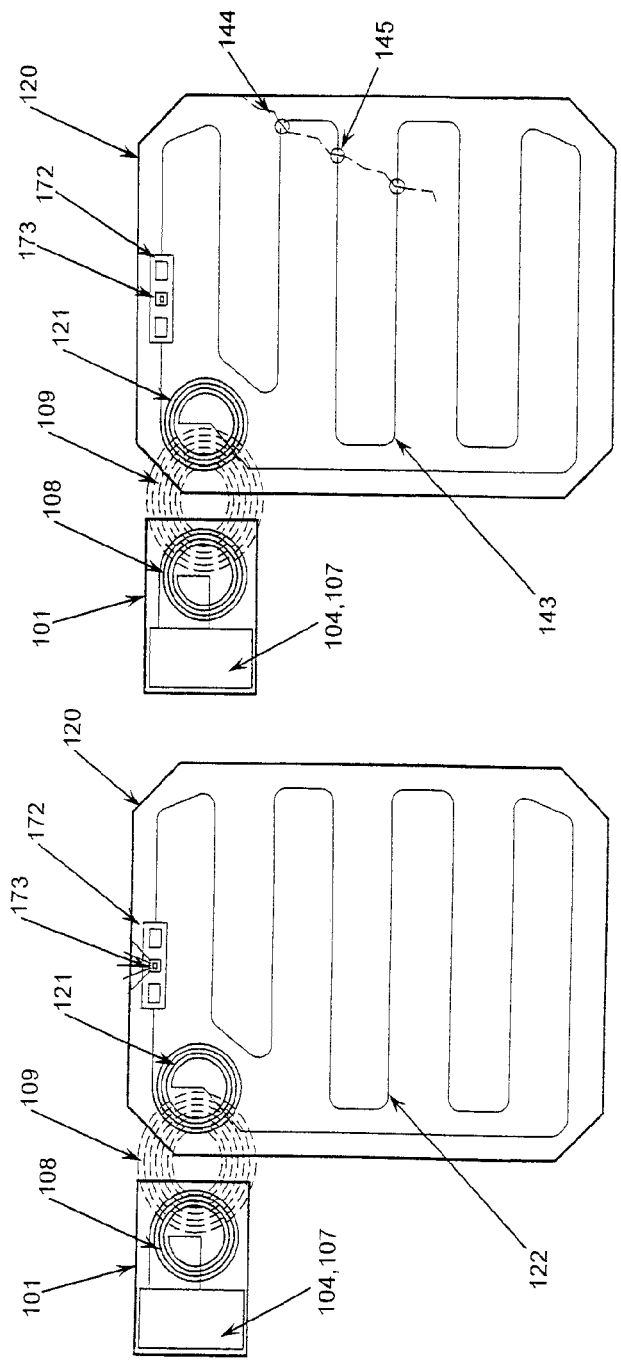
FIG. 11A illustrates a ceramic plate having a closed or continuous conductive trace that provides a positive plate integrity indicator output, an energized LED, when the secondary inductive coil receives power from an interrogator.
FIG. 11B is a plate, trace and coil of FIG. 11A wherein the secondary coil is again energized by the interrogator, however a crack in the ceramic plate creates a crack and thus open circuit in the conductive trace resulting in a negative plate integrity response indicated by no LED indicator output when the secondary inductive coil receives power.

FIGS. 11A and 11B are diagrams that show ceramic plates (120) with conductive integrity circuits (122) receiving inductive power via an alternating magnetic flux coupling (109) to the secondary inductive coil (121) from the primary inductive coil (108) contained within the interrogator unit (101). In FIG. 11A the ceramic has no cracks and the conductive trace (122) placed upon it is continuous or closed, allowing inductive power from the interrogator unit (101) to be provided to the secondary coil (121) and indicator board (172), energizing the LED (173). FIG. 11B shows a ceramic (120) with a fracture (144) that has created breaks (145) in the conductive trace. Although the secondary coil (121) is energized, the break (145) in the conductive trace (143) caused by the fracture (144) in the ceramic creates an open circuit and the indicator LED (173) does not light. To provide the user with additional confidence that the plate being inspected is receiving power through the fabric and outer covers of the plate, a power 'good' sub-circuit on the indicator board does not pass through the conductive trace. When the hard armor plate is damaged and the ceramic is cracked, the power transfer confirmation circuit which is constructed of more substantial micro-flex substrate is more robust than the conductive trace and continues to function. If a plate were to be damaged this circuit and power 'good' LED would identify to the user that inductive power was being transferred to the plate successfully, and that the ceramic integrity indicator LED was not lighting due to the conductive trace being broken.

Figure 12:
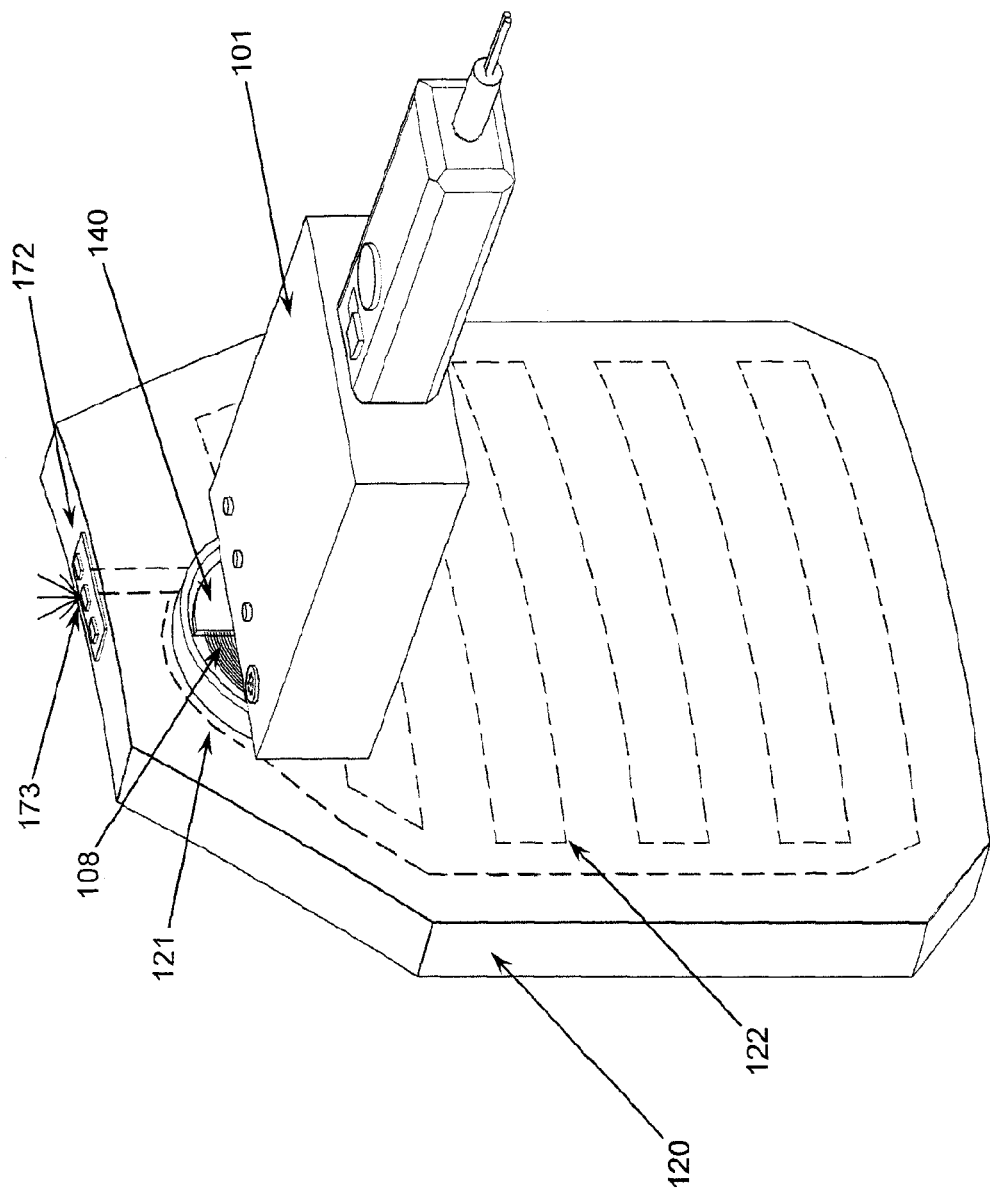
FIG. 12 is a diagram of an interrogator unit positioned 1-2 cm away from the surface of the hard armor plate with the primary inductive coil assembly oriented perpendicular to the hand grip. Indicator LED's on the top of the plate indicate to the user if the ceramic component of the hard armor plate is good or is damaged when power is transmitted from the interrogator unit to the plate.

A handheld interrogator (101) where the primary coil (108) and ferrite backing (140) have been rotated and are perpendicular to the central axis of the unit is shown in FIG. 12. To conduct an inspection the interrogator is brought to within 0-2 cm of the hard armor plate (120), shown without its outer cover, where the proximity detector senses the secondary coil (121) and provides power through the secondary coil and conductive trace (122) to the indicator board (172), located on the top edge of the plate with and LED (176) which indicates the plate is good.

Figure 13A:
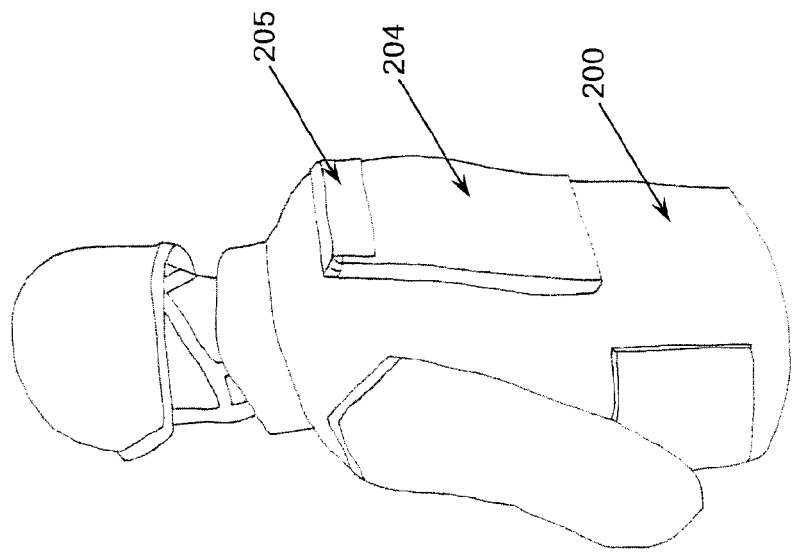
FIG. 13a is, in front perspective view, a soldier wearing a tactical vest having an internal pocket on the front of the vest within which internal pocket is mounted a ceramic armor plate.
Figure 13B:
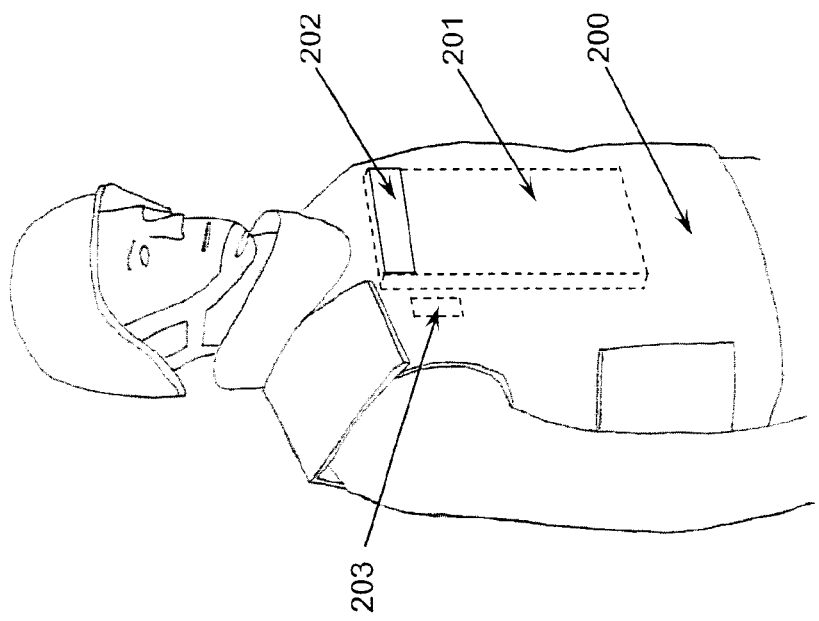
FIG. 13b is, in rear perspective view, the soldier and vest of FIG. 13a showing the vest having an external pocket on the back of the vest within which external pocket is mounted a second armor plate.

As seen in FIGS. 13a and 13b, ballistic protective vest 200 may have front and rear pockets into which are snugly mounted ceramic armor plates. Each of the pockets may be internal or external in the sense that the pleating of the pocket allows expansion to accommodate the plate either internally of the vest or externally of the vest. By way of example, an internal pocket 201 (shown in dotted outline) having an external flap 202 is shown in FIG. 13a, and an external pocket 204 having a flap closure 205 is shown in FIG. 13b. Interrogator primary circuit 203 (also shown in dotted outline in FIG. 13a) may be mounted within the vest. The use of the internal pocket allows for the use of other external conventional pockets on the outside of the vest. Typically the ceramic plate is a tight fit within its vest pocket.

In use, the vest is removed by the soldier at the end of the day. This provides an opportunity to inspect the ceramic plate using the wireless damage detection described herein, for example from the inside cavity of the vest, that is the cavity normally occupied by the soldier's torso. This allows for inspection when the front of the vest is covered with conventional load-carriage pockets such as would be mounted to conventional PALS system webbing.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A system for the wireless detection of damage in a body armor ceramic plate, the system comprising:
   an interrogator,
   a body armor ceramic plate,
   wherein said interrogator includes an inductive primary coil having a resonant frequency and wherein said plate includes a corresponding inductive secondary coil adapted to cooperate with said primary coil when said interrogator is positioned in an interrogation position wirelessly adjacent said plate, and wherein, when in said interrogation position, said primary and secondary coils are inductively coupled in an inductive coupling when said primary coil is energized at said resonant frequency,
   and wherein said plate includes at least one self-contained frangible continuity circuit electrically connected to said secondary coil,
   wherein said inductive coupling induces an electrical current flow in said continuity circuit when said circuit is undamaged and thereby said plate has a non-damaged status,
   a detector cooperating with said primary and secondary coils when said interrogator is in said interrogation position, and wherein said detector detects said inductive coupling and wherein an indicator cooperating with said detector indicates said non-damaged status of said ceramic plate upon said detection of said inductive coupling,
   and wherein said ceramic plate and said self contained continuity circuit do not contain and do not have mounted thereon physical external electrical connectors external to said plate and electrically connected thereto.

2. The system of claim 1 wherein said interrogator further includes a tuned resonant tank circuit which includes said primary coil, said resonant tank circuit having a resonant frequency at a first resonant frequency, and wherein said inductive coupling is mutually inductive such that the impedance and inductance of said secondary coil in said continuous frangible continuity circuit detectably shifts said resonant frequency from said first resonant frequency, and wherein said detector includes a micro-processor to detect said shift of said resonant frequency.

3. The system of claim 2 wherein said detector is mounted in said interrogator, and wherein said interrogator includes a primary drive circuit driving said primary coil within said tank circuit at said resonant frequency.

4. The system of claim 1 wherein said interrogator further includes a tuned resonant tank circuit which includes said primary coil, wherein said resonant tank circuit has a characteristic property which has a first self inductive value when said primary and secondary coils are not said inductively coupled to each other, and wherein said inductive coupling is mutual induction, and wherein when said primary and secondary coils are said inductively coupled, such that said electrical current flow is said induced in said continuity circuit, said first inductive value property detectably shifts said resonant frequency of said tank circuit from said first self inductive value.

5. The system of claim 4 wherein said detector includes a micro processor to detect said shift.

6. The system of claim 5 wherein said detector is mounted in said interrogator, and wherein said interrogator includes a primary drive circuit driving said primary coil within said tank circuit at said resonant frequency.

7. The system of claim 1 wherein said at least one self-contained frangible continuity circuit includes a plurality of said continuity circuits.

8. The system of claim 7 wherein said secondary coil includes a plurality of secondary coils, each secondary coil of said plurality of secondary coils electrically connected to only a corresponding said continuity circuit of said plurality of said continuity circuits.

9. The system of claim 7 wherein said interrogator further includes a tuned resonant tank circuit which includes said primary coil, said resonant tank circuit having a resonant frequency at a first resonant frequency, and wherein said inductive coupling is mutually inductive such that the impedance and inductance of said secondary coil in said continuous frangible continuity circuit detectably shifts said resonant frequency from said first resonant frequency, and wherein said detector includes a micro-processor to detect said shift of said resonant frequency.

10. The system of claim 9 wherein said detector is mounted in said interrogator, and wherein said interrogator includes a primary drive circuit driving said primary coil within said tank circuit at said resonant frequency.

11. The system of claim 7 wherein said interrogator further includes a tuned resonant tank circuit which includes said primary coil, wherein said resonant tank circuit has a characteristic self inductive property which has a first value when said primary and secondary coils are not said inductively coupled to each other, and wherein said inductive coupling is mutual induction, and wherein when said primary and secondary coils are said inductively coupled, such that said electrical current flow is said induced in said continuity circuit, said first inductive value property detectably shifts said resonant frequency of said tank circuit from said first self inductive value.

12. The system of claim 11 wherein said detector includes a micro processor to detect said shift.

13. The system of claim 12 wherein said detector is mounted in said interrogator, and wherein said interrogator includes a primary drive circuit driving said primary coil within said tank circuit at said resonant frequency.

14. The system of claim 1 wherein said interrogator is hand-held and said indicator is mounted in said interrogator.

15. The system of claim 14 wherein said interrogator further includes a tuned resonant tank circuit which includes said primary coil, said resonant tank circuit having a resonant frequency at a first resonant frequency, and wherein said inductive coupling is mutually inductive such that the impedance and inductance of said secondary coil in said continuous frangible continuity circuit detectably shifts said resonant frequency from said first resonant frequency, and wherein said detector includes a micro-processor to detect said shift of said resonant frequency.

16. The system of claim 15 wherein said detector is mounted in said interrogator, and wherein said interrogator includes a primary drive circuit driving said primary coil within said tank circuit at said resonant frequency.

17. The system of claim 14 wherein said interrogator further includes a tuned resonant tank circuit which includes said primary coil, wherein said resonant tank circuit has a characteristic self inductive property which has a first value when said primary and secondary coils are not said inductively coupled to each other, and wherein said inductive coupling is mutual induction, and wherein when said primary and secondary coils are said inductively coupled, such that said electrical current flow is said induced in said continuity circuit, said first inductive value property detectably shifts said resonant frequency of said tank circuit from said first self inductive value.

18. The system of claim 17 wherein said detector includes a micro processor to detect said shift.

19. The system of claim 18 wherein said detector is mounted in said interrogator, and wherein said interrogator includes a primary drive circuit driving said primary coil within said tank circuit at said resonant frequency.

20. The system of claim 1 wherein said interrogator is embedded in a tactical vest, and wherein said ceramic plate is mounted in said tactical vest.

21. The system of claim 20 wherein said interrogator further includes a tuned resonant tank circuit which includes said primary coil, said resonant tank circuit having a resonant frequency at a first resonant frequency, and wherein said inductive coupling is mutually inductive such that the impedance and inductance of said secondary coil in said continuous frangible continuity circuit detectably shifts said resonant frequency from said first resonant frequency, and wherein said detector includes a micro-processor to detect said shift of said resonant frequency.

22. The system of claim 21 wherein said detector is mounted in said interrogator, and wherein said interrogator includes a primary drive circuit driving said primary coil within said tank circuit at said resonant frequency.

23. The system of claim 20 wherein said interrogator further includes a tuned resonant tank circuit which includes said primary coil, wherein said resonant tank circuit has a characteristic self inductive property which has a first value when said primary and secondary coils are not said inductively coupled to each other, and wherein said inductive coupling is mutual induction, and wherein when said primary and secondary coils are said inductively coupled, such that said electrical current flow is said induced in said continuity circuit, said first inductive value property detectably shifts said resonant frequency of said tank circuit from said first self inductive value.

24. The system of claim 23 wherein said detector includes a micro processor to detect said shift.

25. The system of claim 24 wherein said detector is mounted in said interrogator, and wherein said interrogator includes a primary drive circuit driving said primary coil within said tank circuit at said resonant frequency.

26. A system for the wireless detection of damage in a body armor ceramic plate, the system comprising:
an interrogator,
a body armor ceramic plate,
wherein said interrogator includes an inductive primary coil having a resonant frequency and wherein said plate includes a corresponding inductive secondary coil adapted to cooperate with said primary coil when said interrogator is positioned in an interrogation position wirelessly adjacent said plate, and wherein, when in said interrogation position, said primary and secondary coils are inductively coupled in an inductive coupling when said primary coil is energized at said resonant frequency to thereby transfer power to said secondary coil, and wherein said plate includes at least one self-contained frangible continuity circuit electrically connected to said secondary coil, wherein said inductive coupling induces an electrical current flow in said continuity circuit when said circuit when said continuity circuit is undamaged, a detector cooperating with said primary and secondary coils when said interrogator is in said interrogation position, and wherein said detector detects said inductive coupling and wherein an indicator cooperating with said detector indicates said non-damaged status of said ceramic plate upon said detection of said inductive coupling, and wherein said ceramic plate and said self contained continuity circuit do not contain and do not have mounted thereon physical external electrical connectors external to said plate and electrically connected thereto.

27. The system of claim 26 wherein said detector and said indicator and an associated indicator circuit are mounted on said ceramic plate and are electrically connected to said secondary coil and said continuity circuit, and wherein said inductive coupling of said primary and secondary coils transfers said power via said secondary coil to said continuity circuit and said indicator circuit when said continuity circuit is undamaged thereby allowing said electrical current flow through the indicator circuit.

28. The system of claim 27 further comprising a conditioning circuit electrically connected to said secondary coil, said detector and said continuity circuit.

29. The system of claim 28 wherein said ceramic plate has opposite front and back surfaces, and wherein any of said secondary coil, said conditioning circuit, said detector, said continuity circuit are mounted on said back surface, and wherein said front surface is strike surface of said plate.

30. The system of claim 29 wherein all of said secondary coil, said conditioning circuit, said detect, said continuity circuit, said detector, said continuity circuit are mounted on said back surface.

31. The system of claim 26 wherein said at least one self-contained frangible continuity circuit includes a plurality of said continuity circuits.

32. The system of claim 31 wherein said secondary coil includes a plurality of secondary coils, each secondary coil of said plurality of secondary coils electrically connected to only a corresponding said continuity circuit of said plurality of said continuity circuits.

33. The system of claim 26 wherein said interrogator is embedded in a tactical vest, and wherein said ceramic plate is mounted in said tactical vest.

* * * * *